United States Patent [19]
Zedda et al.

[11] Patent Number: 6,117,995
[45] Date of Patent: Sep. 12, 2000

[54] PREPARATION OF STERICALLY HINDERED AMINE ETHERS

[75] Inventors: Alessandro Zedda, Casalecchio di Reno; Gianluca Ferri, Anzola Emilia; Massimiliano Sala, Modena, all of Italy

[73] Assignee: Ciba Specialty Chemicals Corporation, Tarrytown, N.Y.

[21] Appl. No.: 09/253,161

[22] Filed: Feb. 19, 1999

[30] Foreign Application Priority Data

Feb. 25, 1998 [IT] Italy .................................. MI98A0366

[51] Int. Cl.$^7$ ...................... C07D 403/00; C07D 237/00; C07D 241/02; C07D 211/36; C08L 5/48

[52] U.S. Cl. .......................... 544/207; 544/231; 544/357; 544/360; 544/194; 546/188; 546/189; 546/225; 524/91; 524/100; 524/120

[58] Field of Search ................................... 544/207, 231, 544/357, 360, 194; 546/188, 189, 225; 524/100, 91, 120

[56] References Cited

U.S. PATENT DOCUMENTS

| | | | |
|---|---|---|---|
| 4,921,962 | 5/1990 | Galbo et al. | 546/184 |
| 5,204,473 | 4/1993 | Winter et al. | 546/188 |
| 5,489,683 | 2/1996 | Borzatta et al. | 544/209 |
| 5,496,875 | 3/1996 | Borzatta et al. | 526/263 |
| 5,538,840 | 7/1996 | Van Toan et al. | 430/5.2 |
| 5,541,274 | 7/1996 | Steinmann | 524/99 |
| 5,844,026 | 12/1998 | Galbo et al. | 524/100 |

FOREIGN PATENT DOCUMENTS

| | | |
|---|---|---|
| 0 638 617 | 2/1995 | European Pat. Off. . |
| 0 723 990 | 7/1996 | European Pat. Off. . |
| 0 792 911 | 2/1997 | European Pat. Off. . |
| 0 782 994 | 7/1997 | European Pat. Off. . |
| 9-288339 | 11/1997 | Japan . |
| 9-292682 | 11/1997 | Japan . |
| 1006820 | 2/1998 | Netherlands . |
| 2 310 410 | 2/1998 | United Kingdom . |
| 98/33760 | 8/1998 | WIPO . |
| 98/54173 | 12/1998 | WIPO . |
| 98/54174 | 12/1998 | WIPO . |
| 98/54175 | 12/1998 | WIPO . |
| 98/54176 | 12/1998 | WIPO . |
| 98/54177 | 12/1998 | WIPO . |

OTHER PUBLICATIONS

Chemical Abst. 127:248871 of EP 782 994, 1996.
Derwent Abst. 96–343510/35 of EP 723 990, 1996.
Derwent Abst. 95–076334/11 of EP 638 617, 1995.
Walchuk et al, Polymer Preprints, vol. 39, No. 1, Mar. 1998, pp. 296–297.
Nakamura et al, J. Org. Chem., vol 62, No. 16, (1997), pp. 5578–5582.
Nakamura et al., Macromolecules, 1997, 30, pp. 2843–2847.
Bolsman et al., Recueil. Journal of the Royal Netherlands Chemical Society, 97/12, Dec. 1998, pp. 313–319, 1978.
Lee et al., J. Org. Chem. vol. 43, (1978), pp. 4226–4231.
Patel et al., J. Chem Soc. Perkin Trans. 1, (1990) pp. 2729–2731.
Majumdar et al., J. Org. Chem., 62, (1997), pp. 1506–1508.
J. March, Advanced Organic Chemistry, IV Ed., p. 1018, Wiley, 1992.
Kurumada et al., J. Polym. Sci.: Poly. Chem. Ed., vol. 22, pp. 277, 281, (1984).
Chem. Abstr. vol. 16, pp. 2674–2675 for Chem. Ber. 55, pp. 513–522, (1922).
Chem. Ber. 55, pp. 513–522, (1922).
Chem. Ber. 52, pp. 1667–1677, (1919).
Chem. Abstr. 128:68433 for JP 9288339, 1997.
Chem. Abstr. 128:68442 for JP 9292682, 1997.

*Primary Examiner*—Richard L. Raymond
*Assistant Examiner*—Tamthom N. Truong
*Attorney, Agent, or Firm*—Luther A. R. Hall; Tyler A. Stevenson

[57] ABSTRACT

A new process is described for the preparation of a compound of the formula I

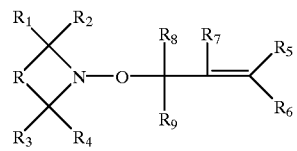

(I)

wherein $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_2$cycloalkyl, or $R_3$ and $R_4$ together with the carbon atom they are attached to are $C_5$–$C_{12}$cycloalkyl; $R_5$, $R_6$, $R_7$, $R_8$ and $R_9$, independently of each other, are H, $C_1$–$C_8$alkyl, $C_2$–$C_8$alkenyl, $C_5$–$C_{12}$aryl, $C_1$–$C_4$haloalkyl, an electron withdrawing group, or $C_6$–$C_{12}$aryl which is substituted by a residue selected from $C_1$–$C_4$alkyl, $C_1$–$C_4$alkoxy, halogen; and $R_7$ and $R_8$ together may also form a chemical bond; and R is an organic linking group containing 2–500 carbon atoms and forming, together with the carbon atoms it is directly connected to and the nitrogen atom, a substituted, 5-, 6 or 7-membered cyclic ring structure; characterized in that a compound of the formula II

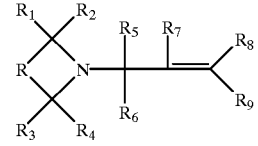

(II)

is oxidized. The compound of the formula I can be hydrogenated and/or halogenated by conventional methods.

Compounds of the formula I and the corresponding hydrogenated and/or halogenated compounds are well suitable as stabilizers for organic material against degradation by light, oxygen and/or heat or yellowing; some are also active as flame retardants.

7 Claims, No Drawings

PREPARATION OF STERICALLY HINDERED AMINE ETHERS

The invention relates to a new process for the preparation of sterically hindered amine ethers, new compounds of this class, their use as stabilizers for organic material against degradation by light, oxygen and/or heat and corresponding compositions.

A number of publications describe the stabilization of organic material using specific sterically hindered amine (HALS) compounds as stabilizers. A valuable class of sterically hindered amines are compounds wherein the nitrogen atom is part of a heterocyclic ring and the nitrogen atom carries an additional organic substituent linked over an oxygen atom (NOR-HALS; Kurumada et al., J. Polym. Sci, Poly. Chem. Ed. 22, 277–81 (1984); U.S. Pat No. 5,204, 473); the oxygen-linked substituent is introduced in these compounds by etherification of the free oxyl- or hydroxylamine with suitable agents.

Some N-allyl nitroxides rearrange under certain conditions into amine ethers (Meisenheimer rearrangement; Chem. Ber. 52, 1667 (1919); Chem. Ber. 55, 513 (1922)). Cleavage of the nitroxide with formation of alkene and hydroxylamine (Cope elimination) is a competing reaction, the rate of which increases with increasing steric hindrance (J. March, Advanced Organic Chemistry, IV Ed., Wiley, 1992).

Now it has been found that, surprisingly, oxidation of a 1-allyl-substituted sterically hindered amine effectively leads to the corresponding 1-allyloxy-substituted product. The invention therefore pertains to a process for the preparation of a compound of the formula I

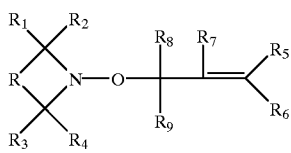

(I)

wherein $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; $R_5$, $R_6$, $R_7$, $R_8$ and $R_9$, independently of each other, are H, $C_1$–$C_8$alkyl, $C_2$–$C_8$alkenyl, $C_5$–$C_{12}$aryl, $C_1$–$C_4$haloalkyl, an electron withdrawing group, or $C_6$–$C_{12}$aryl which is substituted by a residue selected from $C_1$–$C_4$alkyl, $C_1$–$C_4$alkoxy, halogen; and $R_7$ and $R_8$ together may also form a chemical bond; and R is an organic linking group containing 2–500 carbon atoms and forming, together with the carbon atoms it is directly connected to and the nitrogen atom, a substituted, 5-, 6- or 7-membered cyclic ring structure; R preferably being a $C_2$–$C_{500}$hydrocarbon optionally containing 1–200 hetero atoms selected from nitrogen, oxygen, phosphorus, sulfur, silicon and halogen, and, characterized in that a compound of the formula II

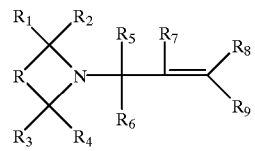

(II)

wherein all residues R and $R_1$–$R_9$ are as defined for formula I, is oxidized.

$R_7$ and $R_8$ together as a chemical bond form an allenic double bond in formula 1, and a triple bond in formula II.

In the compounds of formula I and II and further products, $R_1$, $R_2$, $R_3$ and $R_4$ independently preferably are methyl or ethyl, especially methyl. $R_5$, $R_6$, $R_7$, $R_8$ and $R_9$ as an electron withdrawing group include —CN, nitro, halogen or —COOR$_{10}$ where $R_{10}$ is $C_1$–$C_{12}$alkyl, $C_5$–$C_{12}$cycloalkyl, $C_7$–$C_9$phenylalkyl or phenyl. Preferred as electron withdrawing group are —CN or —COOR$_{10}$ where $R_{10}$ is $C_1$–$C_{12}$alkyl, $C_5$–$C_{12}$cycloalkyl or phenyl, especially wherein $R_{10}$ is $C_1$–$C_{12}$alkyl or cyclohexyl. Preferably, $R_5$, $R_6$, $R_7$, $R_8$ and $R_9$ independently are H or methyl, especially H. Also preferred are compounds wherein $R_5$ and $R_6$ independently are H or methyl, especially H, and $R_7$, $R_8$ and $R_9$ independently are haloalkyl, phenyl, vinyl, nitro, CN, COOR$_{10}$, or $R_7$ and $R_8$ together form a chemical bond.

Further preferences for the linking group R are mainly as described below for products of formulae III, IV and V.

Of special importance is a process for the preparation of a compound of the formula I by oxidation of a compound of the formula II, wherein $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; $R_5$, $R_6$, $R_7$, $R_8$ and $R_9$, independently of each other, are H, $C_1$–$C_8$alkyl, $C_3$–$C_8$alkenyl, $C_5$–$C_{12}$aryl, an electron withdrawing group, $C_6$–$C_{12}$aryl which is substituted by $C_1$–$C_4$alkyl, $C_1$–$C_4$alkoxy, halogen; and R is a $C_3$–$C_{500}$hydrocarbon optionally containing 1–200 hetero atoms selected from nitrogen, oxygen, phosphorus, sulfur and halogen, and forming, together with the two carbon and the nitrogen atom, a substituted, 6-membered cyclic ring structure.

Aryl stands for a group obeying the Debye-Hueckel rule; preferred as $C_6$–$C_{12}$aryl are phenyl and naphthyl.

Alkyl is a branched or unbranched radical, embracing, within the definitions given, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

Alkanoyl is alkyl connected over a carbonyl linkage; thus, $C_2$–$C_{20}$alkanoyl includes acetyl, propionyl, butyryl, hexanoyl, steaoryl.

Haloalkyl is alkyl substituted by halogen, e.g. 1 or 2 halogen atoms. Halogen atoms are preferably chloro or bromo, especially bromo.

Cycloalkyl is a saturated monovalent monocyclic hydrocarbon residue, e.g. cyclopentyl, cyclohexyl, cycloheptyl, cyclooctyl, cyclododecyl; preferred is cyclohexyl.

Organic residues or hydrocarbons containing heteroatoms, such as alkyl or alkylene interrupted by hetero groups like oxygen or NH, usually contain these heteroatoms as typical functional groups like oxo, oxa, hydroxy, carboxy, ester, amino, amido, nitro, nitrilo, isocyanato, fluoro, chloro, bromo, phosphate, phosphonate, phosphite, silyl, thio, sulfide, sulfinyl, sulfo, heterocyclyl including pyrrolyl, indyl, carbazolyl, furyl, benzofuryl, thiophenyl, benzothiophenyl, pyridyl, chinolyl, isochinolyl, pyridazinyl, pyrimidinyl, pyrazinyl, triazolyl, benzotriazolyl, triazinyl, pyrazolyl, imidazolyl, thiazolyl, oxazolyl, and corresponding saturated and/or substituted groups like, for example, piperidyl, piperazinyl, morpholinyl etc. They may be interrupted by one or more of these groups; usually there are no linkages of the type O—O O—N (except nitro, cyanato, isocyanato, nitroso), N—N (except in heterocyclic ring structures), N—P or P—P present, regardless of the order.

Preferably, in organic residues or hydrocarbons containing heteroatoms such as R there is not more than one heteroatom attached by a single bond to the same carbon atom. A spacer consisting of one or more heteroatoms usually is embedded in a carbon chain or ring or inserted into a carbon-hydrogen bond.

Compounds of the formula I can be monomeric or polymeric. They contain 1 or more groups of the formula I'

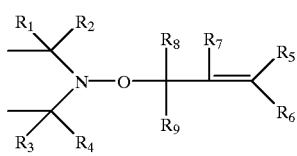

(I')

In case that the compounds of the formula I' are polymeric, they contain a group of the formula I' in the repeating structural unit.

Starting compounds of the formula II are known in the art or can be obtained in analogy to known compounds. Present process can start from isolated compounds of the formula 11 or can use the solution of these starting compounds as obtained directly after synthesis.

In the process of present invention, the oxidation reaction can be carried out using known oxidants, e.g. oxygen, peroxides or other oxidizing agents such as nitrates, permanganates, chlorates; preferred are peroxides, such as hydrogen peroxide based systems, especially peracids such as perbenzoic acid or peracetic acid. The oxidant is conveniently used in stoiciometric amount or in excess, e.g. using 1–2 moles active oxyen atoms for each group of the formula I' in the desired product.

The reaction can be carried out in the presence of a suitable solvent, for example an aromatic or aliphatic hydrocarbon, alcohol, ester, amide, ether, or halogenated hydrocarbon; examples are benzene, toluene, xylene, mesitylene, methanol, ethanol, propanol, butanol, dimethylformamide, dimethylsulfoxide, methylene chloride; preferred is a $C_1$–$C_4$alcohol, benzene, toluene, xylene, or chlorinated $C_1$–$C_6$hydrocarbon.

Temperature and pressure are not critical and depend mainly on the oxidant system used; preferably, temperature is kept during the reaction in the range between –20° C. and +40° C. Conveniently, the pressure is kept close to atmospheric pressure, e.g. between 0.5 and 1.5 bar; when oxidation is achieved with gaseous oxygen, the pressure of oxygen or oxygen/inertgas may exceed atmospheric pressure.

The process of present invention can be followed by further process steps known in the art, e.g. hydrogenation of an ethylenic double bond, halogenation, e.g. bromination, of an ethylenic double bond and/or polymerization, with or without previous isolation of the product of formula I.

Hydrogenation of the ethylenic double bond (carbon—carbon double bond) in the compound of the formula I can be achieved by methods known in the art, e.g. reaction with gaseous hydrogen under catalytic conditions or reaction with hydrogenating agents. Preferred is catalytic hydrogenation; known catalysts can be employed such as Pt, Pt, Pd, Ni, Ru, Rh, on support such as carbon or without support, Raney-Ni etc.

Hydrogenation of an allenic double bond in a compound of formula I wherein $R_7$ and $R_8$ together are a chemical bond, proceeds in 2 steps. The first step leads to a partly hydrogenated product, which may be isolated or subjected to further derivatization, and which corresponds to formula IV

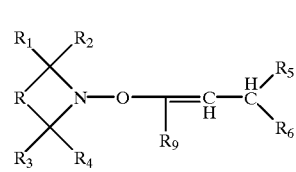

(IV)

where R, $R_1$–$R_6$ and $R_9$ are as defined above.

Complete hydrogenation yields a product of the formula III

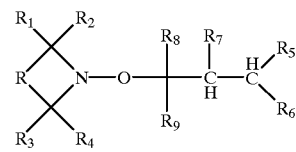

(III)

where R, $R_1$–$R_6$ and $R_9$ are as defined above for formula I and $R_7$ and $R_8$ are H, $C_1$–$C_8$alkyl, $C_3$–$C_8$alkenyl, $C_5$–$C_{12}$aryl, $C_1$–$C_4$haloalkyl, an electron withdrawing group, or $C_6$–$C_{12}$aryl which is substituted by a residue selected from $C_1$–$C_4$alkyl, $C_1$–$C_4$alkoxy, halogen.

Halogenation is another follow-up reaction which may be carried out subsequent to the process of present invention, mainly according to methods known in the art and using the appropriate reactant, e.g. as summarized in J. March, Advanced Organic Chemistry: Reaction mechanisms and Structure, 4th Edn., Wiley, 1992, p. 812. Halogen thereby is added to the carbon—carbon double bond of a compound of formula I or IV, resulting in an α, β-dihalogenated product. The halogen reagent $X_2$, where X is F, Cl, Br, I or preferably Cl or Br, especially Br, can be applied in gaseous, liquid or solid form, pure or as a solution. Halogen can also be released during the reaction in appropriate amounts using a suitable carrier substance or source.

Reactions can be carried out according to methods known in the art using hydrogen pressures in the common range, preferably between 0.5 and about 200 bar, especially between 1 and 100 bar (1 bar=$10^5$ Pa). Reactions can be carried out using suitable solbents, e.g. water, hydrocarbons like hexane, petrol fractions, toluene, xylene, esters, ethers, halogenated hydrocarbons or alcohols like methanol or ethanol. Reactions can also be carried out without solvent. Temperatures are uncritical and are mainly in the range between –10° C. and about 150° C., e.g. between 0° C. and the boiling point of the solvent like the range 0–100° C. or 20–80° C.

Present invention therefore also pertains to a process for the preparation of a compound of the formula V

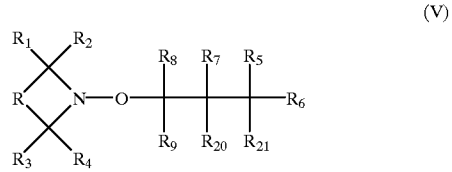

(V)

wherein R, $R_1$, $R_2$, $R_3$ and $R_4$, $R_5$, $R_6$, and $R_9$ are as defined for formula 1, $R_7$ and $R_8$ are H, $C_1$–$C_8$alkyl, $C_3$–$C_8$alkenyl, $C_5$–$C_{12}$aryl, $C_1$–$C_4$haloalkyl, halogen, an electron withdrawing group, or $C_6$–$C_{12}$aryl which is substituted by a residue selected from $C_1$–$C_4$alkyl, $C_1$–$C_4$alkoxy, halogen; and both of $R_{20}$ and $R_{21}$ are either hydrogen or halogen; characterized in that a compound of the formula II is oxidized and the resulting intermediate of formula I is subjected to hydrogenation and/or halogenation.

The above process can also be carried out in a way wherein the intermediate of formula I is derivatized to become another structure of formula I before subjecting it to hydrogenation and/or halogenation, e.g. by esterification, dimerization, trimerization or polymerization; or wherein the intermediate of formula I is first subjected to hydrogenation, and then further derivatized, e.g. by esterification, dimerization, trimerization or polymerization.

Preferred is a process for the preparation of a compound of the formula V wherein R is an organic linking group containing 2–500 carbon atoms and forming, together with the carbon atoms it is directly connected to and the nitrogen atom, a substituted, 5-, 6 or 7-membered cyclic ring structure; $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; $R_5$, $R_6$, and $R_9$, independently of each other, are H, $C_1$–$C_8$alkyl, $C_3$–$C_8$alkenyl, $C_5$–$C_{12}$aryl, $C_1$–$C_4$haloalkyl, an electron withdrawing group, or $C_6$–$C_{12}$aryl which is substituted by a residue selected from $C_1$–$C_4$alkyl, $C_1$–$C_4$alkoxy, halogen; $R_7$ and $R_8$ are H, $C_1$–$C_8$alkyl, $C_3$–$C_8$alkenyl, $C_5$–$C_{12}$aryl, $C_1$–$C_4$haloalkyl, halogen, an electron withdrawing group, or $C_6$–$C_{12}$aryl which is substituted by a residue selected from $C_1$–$C_4$alkyl, $C_1$–$C_4$alkoxy, halogen; and both of $R_{20}$ and $R_{21}$ are either hydrogen or halogen.

Most preferred products of the process of present invention are of formulae IIIc, IVa and Va described further below.

In general, all products of present process can be used as stabilizers for organic material against detrimental effects of light, oxygen and heat. Of special value are the compounds of formulae I, Ia, II, IV and V. Best results are achieved with compounds of formula IIII wherein R, $R_1$, $R_2$, $R_3$ and $R_4$, are as defined for formula I and $R_5$, $R_6$, $R_7$, $R_8$ and $R_9$, independently of each other, are H, $C_1$–$C_8$alkyl, $C_2$–$C_8$alkenyl, C5–$C_{12}$aryl, CN, $COOR_{10}$, where $R_{10}$ is as defined for formula 1, or are $C_6$–$C_{12}$aryl which is substituted by a residue selected from $C_1$–$C_4$alkyl, $C_1$–$C_4$alkoxy. Organic material most effectively stabilized by present compounds is organic polymeric material described below, e.g. coatings and thermoplastic bulk polymers, films or fibers. Where the polymers come in contact with a pesticide, e.g. a pesticide containing sulfur and/or halogen atoms, the products of present process achieve both a stabilization against light and detrimental effects of the pesticide. This is especially important for polymers, e.g. films, tapes or fibers, used in agricultural applications, mainly polyolefines such as PE or PP or polyolefin copolymers. Preferred compounds in this application are those of formula ll, especially IIIc below.

An important utility for all products of present process is the stabilization of paper and pulp, especially paper or pulp still containing lignin, against yellowing. Application of present products can be done as described, for example, in the international patent application No. WO 98/04381 and the corresponding U.S. patent application Ser. No. 09/119567, and publications cited therein. Most preferred for this application is the use of a monomeric compound of the formula III, e.g. one wherein R is $C_3$–$C_{12}$alkylene, or $C_4$–$C_{12}$alkylene interrupted by O, NH, OCO or NHCO, $R_1$–$R_4$ are methyl or ethyl, especially methyl, and $R_5$–$R_9$ are each H or $C_1$–$C_4$alkyl, especially H; examples are 1-propyloxy-2,2,6,6-tetramethylpiperidine, 1-propyloxy-2,2,6,6-tetramethylpiperidine-4-one, or the product of present example 4a (see below).

Further, the products of present process can be used with advantage as flame retardants for organic polymers. Thus, by using the products of present invention, an organic polymer is stabilized against detrimental effects of light, oxygen and heat, while the same time the inflammability of the polymer is effectively reduced. Application of present products can be done as described, for example, in the international patent application No. WO 98113469 and the corresponding U.S. patent application Ser. No. 09/104718, and publications cited therein, as well as EP-A-792911 or U.S. Pat. No. 5,393,812. Most preferred for this utility is the use of a compound of the formula III or V, especially those of formula IIIc below or of formula V wherein at least one of $R_5$, $R_6$, $R_7$, $R_8$, $R_9$, $R_{20}$ or $R_{21}$ is halogen, especially bromo. Present compounds can be used as flame retardants alone or in combination with known flame retardants like a flame retardant compound selected from the halogenated, phosphorus, boron, silicon and antimony compounds, metal hydroxides, metal hydrates and metal oxides or mixtures thereof.

It has been a further finding of this invention that some compounds of formula III are especially well suitable as stabilizers for organic material against detrimental effects of light, oxygen and heat.

The invention therefore also provides compositions comprising

A) an organic polymer which is sensitive to oxidative, thermal andlor actinic degradation, and B) at least one compound of the formula IIIa, IVa or Va

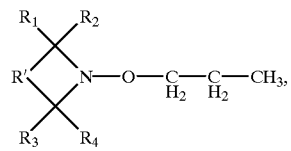

(IIIa)

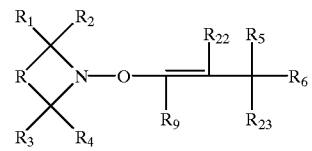

(IVa)

-continued

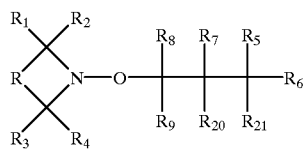
(Va)

wherein

R' and R each is an organic linking group of the formula

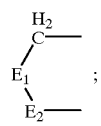
(VI)

$E_2$ is —CO— or —(CH$_2$)$_p$—, where p is 0, 1 or 2; $E_1$ is a carbon atom carrying the two residues $R_{24}$ and $R_{25}$, or is >N—$R_{25}$, or is oxygen, and $R_{24}$ and $R_{25}$ are hydrogen or an organic residue, characterized in that the linking group R in total contains 2–500 carbon atoms and forms, together with the carbon atoms it is directly connected to it and the nitrogen atom, a substituted, 5-, 6 or 7-membered cyclic ring structure; $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; $R_5$, $R_6$, $R_7$, $R_8$ and $R_9$, independently of each other, are H, $C_1$–$C_8$alkyl, $C_2$–$C_8$alkenyl, $C_5$–$C_{12}$aryl, $C_1$–$C_4$haloalkyl, an electron withdrawing group, or $C_6$–$C_{12}$aryl which is substituted by a residue selected from $C_1$–$C_4$alkyl, $C_1$–$C_4$alkoxy, halogen; $R_{20}$ and $R_{21}$ are halogen; and $R_{22}$ and $R_{23}$ are hydrogen or together are a chemical bond.

Usually R' in formula IIIa is not the linking group

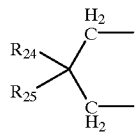

wherein $R_{24}$ is hydrogen and $R_{25}$ is hydrogen or hydroxy.

Preferred is a formula IIa wherein R' is a $C_7$–$C_{500}$hydrocarbon containing 1–200 hetero atoms selected from nitrogen, oxygen, phosphorus, sulfur and halogen, and forming, together with the two carbon and the nitrogen atom, a substituted, 5- or 6-membered cyclic ring structure, and $R_1$, $R_2$, $R_3$ and $R_4$ are as defined above.

Current invention further provides for the use of compounds of the formula IIIa for stabilizing organic polymers against oxidative, thermal or actinic degradation. The invention likewise comprises a method of stabilizing organic polymers against thermal, oxidative and/or actinic degradation, which comprises adding to the polymer at least one compound of the formula IIIa.

More detailed examples of sterically hindered amines are described below under classes (a') to (j').

(a') A compound of the formula (1a)

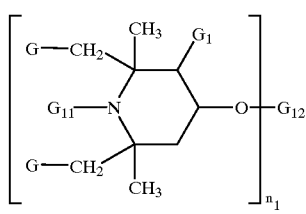
(1a)

in which $n_1$ is a number from 1 to 4, G and $G_1$, independently of one another, are hydrogen or methyl, $G_{11}$ is n-propoxy, O—CH=C=CH$_2$, O—CH=CH—CH$_3$ or halogenated n-propoxy, especially n-propoxy, or brominated n-propoxy;

$G_{12}$, if $n_1$ is 1, is hydrogen, $C_1$–$C_{18}$alkyl which is uninterrupted or interrupted by one or more oxygen atoms, cyanoethyl, benzoyl, glycidyl, a monovalent radical of an aliphatic, cycloaliphatic, araliphatic, unsaturated or aromatic carboxylic acid, carbamic acid or phosphorus-containing acid or a monovalent silyl radical, preferably a radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3 —COO$Z_{12}$ groups, in which $Z_{12}$ is H, $C_1$–$C_{20}$alkyl, $C_3$–$C_{12}$alkenyl, $C_5$–$C_7$cycloalkyl, phenyl or benzyl, $G_{12}$, if $n_1$ is 2, is $C_2$–$C_{12}$alkylene, $C_4$–$C_{12}$alkenylene, xylylene, a divalent radical of an aliphatic, cycloaliphatic, araliphatic or aromatic dicarboxylic acid, dicarbamic acid or phosphorus-containing acid or a divalent silyl radical, preferably a radical of an aliphatic dicarboxylic acid having 2 to 36 carbon atoms, or a cycloaliphatic or aromatic dicarboxylic acid having 8–14 carbon atoms or of an aliphatic, cycloaliphatic or aromatic dicarbamic acid having 8–14 carbon atoms, where each dicarboxylic acid may be substituted in the aliphatic, cycloaliphatic or aromatic moiety by one or two —COO$Z_{12}$ groups, $G_{12}$, if $n_1$ is 3, is a trivalent radical of an aliphatic, cycloaliphatic or aromatic tricarboxylic acid, which may be substituted in the aliphatic, cycloaliphatic or aromatic moiety by —COO$Z_{12}$, of an aromatic tricarbamic acid or of a phosphorus-containing acid, or is a trivalent silyl radical, and $G_{12}$, if $n_1$ is 4, is a tetravalent radical of an aliphatic, cycloaliphatic or aromatic tetracarboxylic acid.

The carboxylic acid radicals mentioned above are in each case taken to mean radicals of the formula (—CO)$_x$R, where x is as defined above, and the meaning of R arises from the definition given.

Alkyl with up to 20 carbon atoms is, for example, methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

Examples of several $G_{12}$ radicals are given below.

If $G_{12}$ is a monovalent radical of a carboxylic acid, it is, for example, an acetyl, caproyl, stearoyl, acryloyl, methacryloyl, benzoyl or β-(3,5-di-tert-butyl-4-hydroxyphenyl)propionyl radical.

If $G_{12}$ is a monovalent silyl radical, it is, for example, a radical of the formula —(C$_j$H$_{2j}$)—Si(Z')$_2$Z", in which j is an integer in the range from 2 to 5, and Z' and Z", independently of one another, are $C_1$–$C_4$alkyl or $C_1$–$C_4$alkoxy.

If $G_{12}$ is a divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl)malonyl or bicycloheptenedicarbonyl radical or a group of the formula

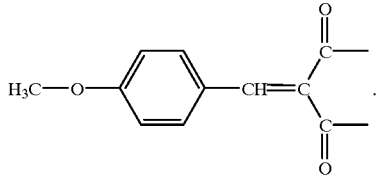

If $G_{12}$ is a trivalent radical of a tricarboxylic acid, it is, for example, a trimellitoyl, citryl or nitrilotriacetyl radical.

If $G_{12}$ is a tetravalent radical of a tetracarboxylic acid, it is, for example, the tetravalent radical of butane-1,2,3,4-tetracarboxylic acid or of pyromellitic acid.

If $G_{12}$ is a divalent radical of a dicarbamic acid, it is, for example, hexamethylenedicarbamoyl or 2,4-toluylenedicarbamoyl radical.

Preference is given to compounds of the formula (1a) in which G and $G_1$ are hydrogen, $G_{11}$ is hydrogen or methyl, $n_1$ is 2 and $G_{12}$ is the diacyl radical of an aliphatic dicarboxylic acid having 4–12 carbon atoms.

(b') A compound of the formula (1b)

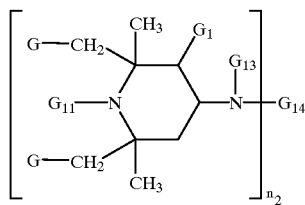

(1b)

in which G and $G_1$, independently of one another, are hydrogen or methyl, $G_{11}$ is n-propoxy, $G_{13}$ is hydrogen, $C_1$–$C_{12}$alkyl, $C_2$–$C_5$hydroxyalkyl, $C_5$–$C_7$cycloalkyl, $C_7$–$C_8$aralkyl, $C_1$–$C_{18}$alkanoyl, $C_3$–$C_5$alkenoyl, benzoyl or a group of the formula (1b-1)

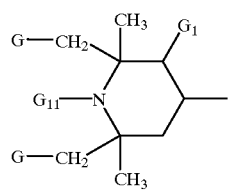

(1b-1)

$n_2$ is the number 1, 2 or 3; and $G_{14}$, if $n_2$ is 1, is hydrogen, $C_1$–$C_{18}$alkyl, $C_3$–$C_8$alkenyl, $C_5$–$C_7$cycloalkyl, $C_1$–$C_4$alkyl which is substituted by a hydroxyl, cyano, alkoxycarbonyl or carbamide group, glycidyl, a group of the formula —CH$_2$—CH(OH)—Z or of the formula —CONH—Z, in which Z is hydrogen, methyl or phenyl;

$G_{14}$, if $n_2$ is 2, is $C_2$–$C_{12}$alkylene, $C_6$–$C_{12}$arylene, xylylene, a —CH$_2$—CH(OH)—CH$_2$ group or a —CH$_2$—CH(OH)—CH$_2$—O—D—O— group, in which D is $C_2$–$C_{10}$alkylene, $C_6$–$C_{15}$arylene, $C_6$–$C_{12}$cycloalkylene, or, provided that $G_{13}$ is not alkanoyl, alkenoyl or benzoyl, $G_{14}$ can alternatively be 1-oxo-$C_2$–$C_{12}$alkylene, a divalent radical of an aliphatic, cycloaliphatic or aromatic dicarboxylic acid or dicarbamic acid or alternatively the group —CO—, $G_{14}$, if $n_2$ is 3, is a group

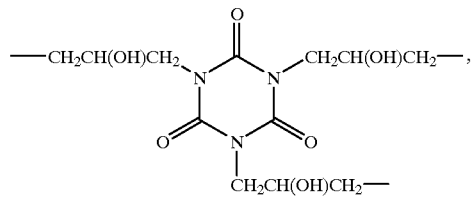

or, if $n_2$ is 1, $G_{13}$ and $G_{14}$ together can be the divalent radical of an aliphatic, cycloaliphatic or aromatic 1,2- or 1,3-dicarboxylic acid.

Some examples for the radicals $G_{13}$, $G_{14}$ and D are given below.

Any alkyl substituents are as defined above for (a').

Any $C_5$–$C_7$cycloalkyl substituents are, in particular, cyclohexyl.

$C_7$–$C_8$aralkyl $G_{13}$ is, in particular, phenylethyl or especially benzyl.

$C_2$–$C_5$hydroxyalkyl $G_{13}$ is, in particular, 2-hydroxyethyl or 2-hydroxypropyl.

$C_1$–$C_{18}$alkanoyl $G_{13}$ is, for example, formyl, acetyl, propionyl, butyryl, octanoyl, dodecanoyl, hexadecanoyl, octadecanoyl, but preferably acetyl, and $C_3$–$C_5$alkenoyl $G_{13}$ is, in particular, acryloyl.

$C_2$–$C_8$alkenyl $G_{14}$ is, for example, allyl, methallyl, 2-butenyl, 2-pentenyl, 2-hexenyl or 2-octenyl.

$G_{14}$ as a hydroxyl-, cyano-, alkoxycarbonyl- or carbamide-substituted $C_1$–$C_4$alkyl can be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

Any $C_2$–$C_{12}$alkylene radicals are, for example, ethylene, propylene, 2,2-dimethylpropylene, tetramethylene, hexamethylene, octamethylene, decamethylene or dodecamethylene. Any $C_6$–$C_{15}$arylene substituents are, for example, o-, m- or p-phenylene, 1,4-naphthylene or 4,4'-diphenylene.

$C_6$–$C_{12}$cycloalkylene is, in particular, cyclohexylene.

$G_{14}$ as 1—oxo—$C_{2-12}$alkylene is preferably a group

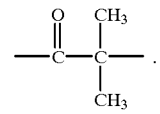

Preference is given to compounds of the formula (1b) in which $n_2$ is 1 or 2, G and $G_1$ are hydrogen, $G_{13}$ is hydrogen, $C_1$–$C_{12}$alkyl or a group of the formula

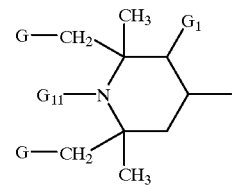

and $G_{14}$, in the case where $n_2=1$, is hydrogen or $C_1$–$C_{12}$alkyl, and, in the case where $n_2=2$, is $C_2$–$C_8$alkylene or 1-oxo-$C_2$–$C_8$alkylene.

(c') A compound of the formula (1c)

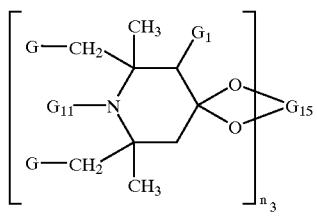

(1c)

in which $n_3$ is the number 1 or 2, G, $G_1$ and $G_{11}$ are as defined under (b'), and $G_{15}$, if $n_3$ is 1, is $C_2$–$C_8$alkylene, $C_2$–$C_8$hydroxyalkylene or $C_4$–$C_{22}$acyloxyalkylene, and if $n_3$ is 2, $G_{15}$ is the (—$CH_2$)$_2$C(CH$_2$—)$_2$ group.

$C_2$–$C_8$alkylene or $C_2$–$C_8$hydroxyalkylene $G_{15}$ is, for example, ethylene, 1-methylethylene, propylene, 2-ethylpropylene or 2-ethyl-2-hydroxymethylpropylene.

$C_4$–$C_{22}$acyloxyalkylene $G_{15}$ is, for example, 2-ethyl-2-acetoxymethylpropylene.

(d') A compound of the formula (1d-1), (1 d-2) or (1 d-3),

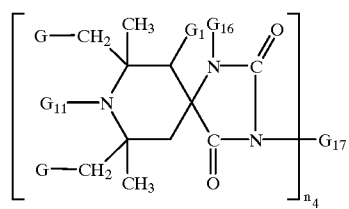

(1d-1)

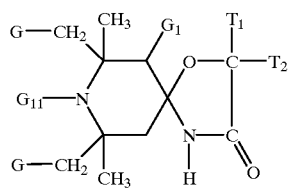

(1d-2)

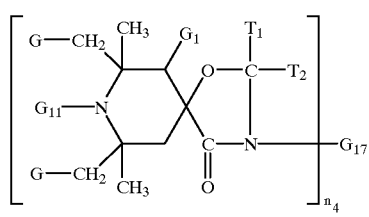

(1d-3)

in which $n_4$ is the number 1 or 2, G, $G_1$ and $G_{11}$ are as defined under (b'), $G_{16}$ is hydrogen, $C_1$–$C_{12}$alkyl, allyl, benzyl, glycidyl or $C_2$–$C_6$alkoxyalkyl, and $G_{17}$, if $n_4$ is 1, is hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_6$–$C_{10}$aryl, glycidyl or a group of the formula —(CH$_2$)$_p$—COO—Q or —(CH$_2$)$_p$—O—CO—Q, in which p is 1 or 2, and Q is $C_1$–$C_4$alkyl or phenyl, and $G_{17}$, if n is 2, is $C_2$–$C_{12}$alkylene, $C_4$–$C_{12}$alkenylene, $C_6$–$C_{12}$arylene, a group of the formula —CH$_2$—CH(OH)—CH$_2$—O—D'—O—CH$_2$—CH(OH)—CH$_2$—, in which D' is $C_2$–$C_{10}$alkylene, $C_6$–$C_{15}$arylene, $C_6$–$C_{12}$cycloalkylene or a group of the formula —CH$_2$CH(OD")CH$_2$—(OCH$_2$–CH(OD")CH$_2$)$_2$—, in which D" is hydrogen, $C_1$–$C_{18}$alkyl, allyl, benzyl, $C_2$–$C_{12}$alkanoyl or benzoyl, $T_1$ and $T_2$, independently of one another, are hydrogen, $C_1$–$C_{18}$alkyl or unsubstituted or halogen- or $C_1$–$C_4$alkyl-substituted $C_6$–$C_{10}$aryl or $C_7$–$C_9$aralkyl, or $T_1$ and $T_2$ together with the carbon atom bonding them form a $C_5$–$C_{14}$cycloalkane ring.

A compound of the formula (1d-3) is preferred.

Some examples of the several variables in the formulae (1d-1), (1 d-2) and (1 d-3) are given below.

Any $C_1$–$C_{12}$alkyl substituents are, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any $C_1$–$C_{18}$alkyl substituents can be, for example, the abovementioned groups and in addition, for example, n-tridecyl, n-tetradecyl, n-hexadecyl or n-octadecyl.

Any $C_2$–$C_6$alkoxyalkyl substituents are, for example, methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

$C_3$–$C_5$alkenyl $G_{17}$ is, for example, 1-propenyl, allyl, methallyl, 2-butenyl or 2-pentenyl.

$C_7$–$C_9$aralkyl $G_{17}$, $T_1$ and $T_2$ are, in particular, phenethyl or especially benzyl. If $T_1$ and $T_2$ together with the carbon atom form a cycloalkane ring, this can be, for example, a cyclopentane, cyclohexane, cyclooctane or cyclododecane ring.

$C_2$–$C_4$hydroxyalkyl $G_{17}$ is, for example, 2-hydroxyethyl, 2-hydroxypropyl, 2-hydroxybutyl or 4-hydroxybutyl.

$C_6$–$C_{10}$aryl $G_{17}$, $T_1$ and $T_2$ are, in particular, phenyl or α- or β-naphthyl, which are unsubstituted or substituted by halogen or $C_1$–$C_4$alkyl.

$C_2$–$C_{12}$alkylene $G_{17}$ is, for example, ethylene, propylene, 2,2-dimethylpropylene, tetramethylene, hexamethylene, octamethylene, decamethylene or dodecamethylene.

$C_4$–$C_{12}$alkenylene $G_{17}$ is, in particular, 2-butenylene, 2-pentenylene or 3-hexenylene.

$C_6$–$C_{12}$arylene $G_{17}$ is, for example, o-, m- or p-phenylene, 1,4-naphthylene or 4,4'-diphenylene.

$C_2$–$C_{12}$alkanoyl D" is, for example, propionyl, butyryl, octanoyl, dodecanoyl, but preferably acetyl.

$C_2$–$C_{10}$alkylene, $C_6$–$C_{15}$arylene or $C_6$–$C_{12}$cycloalkylene D' have, for example, one of the definitions given for D under (b').

(e') A compound of the formula (1e)

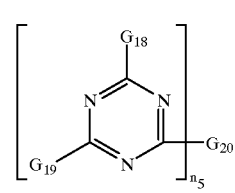

(1e)

in which $n_5$ is the number 1 or 2, and $G_{18}$ is a group of the formula

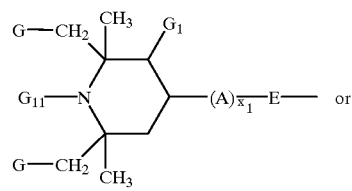

or

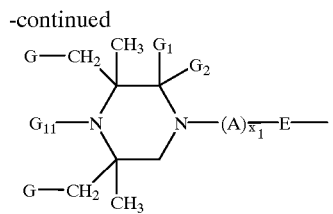

in which G and $G_{11}$ are as defined under (b'), and $G_1$ and $G_2$ are hydrogen, methyl or, together, are a substituent =O, E is —O— or —ND'''—, A is $C_2$–$C_6$alkylene or —(CH$_2$)$_3$—O— and $x_1$ is the number 0 or 1, D''' is hydrogen, $C_1$–$C_{12}$alkyl, $C_2$–$C_5$hydroxyalkyl or $C_5$–$C_7$cycloalkyl, $G_{19}$ is identical to $G_{18}$ or is one of the groups —N($G_{21}$)($G_{22}$), —O$G_{23}$, —N(H)(CH$_2$O$G_{23}$) or —N(CH$_2$O$G_{23}$)$_2$, $G_{20}$, if n=1, is identical to $G_{18}$ or $G_{19}$ and, if n=2, is an —E—D$^{IV}$—E— group, in which D$^{IV}$ is $C_2$–$C_8$alkylene or $C_2$–$C_8$alkylene which is interrupted by 1 or 2-N$G_{21}$- groups, $G_{21}$ is $C_1$–$C_{12}$alkyl, cyclohexyl, benzyl or $C_1$–$C_4$-hydroxyalkyl or a group of the formula

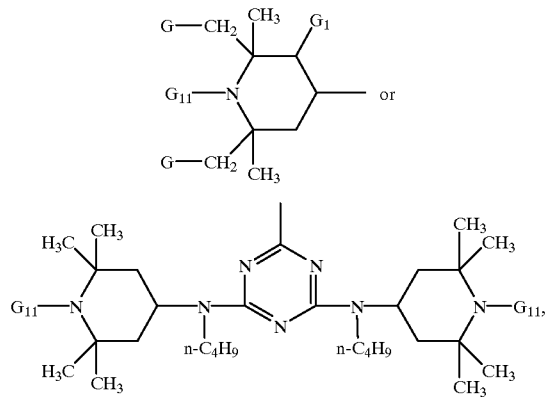

$G_{22}$ is $C_1$–$C_{12}$alkyl, cyclohexyl, benzyl or $C_1$–$C_4$hydroxyalkyl, and $G_{23}$ is hydrogen, $C_1$–$C_{12}$alkyl or phenyl, or $G_{21}$ and $G_{22}$ together are $C_4$–$C_5$alkylene or $C_4$–$C_5$oxaalkylene, for example —CH$_2$CH$_2$—O—CH$_2$CH$_2$—, or a group of the formula —CH$_2$CH$_2$—N($G_{11}$)—CH$_2$CH$_2$—.

Some examples of the several variables in the formula (1e) are given below.

Any $C_1$–$C_{12}$alkyl substituents are, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any hydroxyalkyl substituents are, for example, 2-hydroxyethyl, 2-hydroxypropyl, 3-hydroxypropyl, 2-hydroxybutyl or 4-hydroxybutyl.

Any $C_5$–$C_7$cycloalkyl substituents are, for example, cyclopentyl, cyclohexyl or cycloheptyl. Cyclohexyl is preferred.

$C_2$–$C_6$alkylene A is, for example, ethylene, propylene, 2,2-dimethylpropylene, tetramethylene or hexamethylene.

If $G_{21}$ and $G_{22}$ together are $C_4$–$C_5$alkylene or oxaalkylene, they are, for example, tetramethylene, pentamethylene or 3-oxapentamethylene.

Examples of polyalkylpiperidine compounds from this class are the compounds of the following formulae:

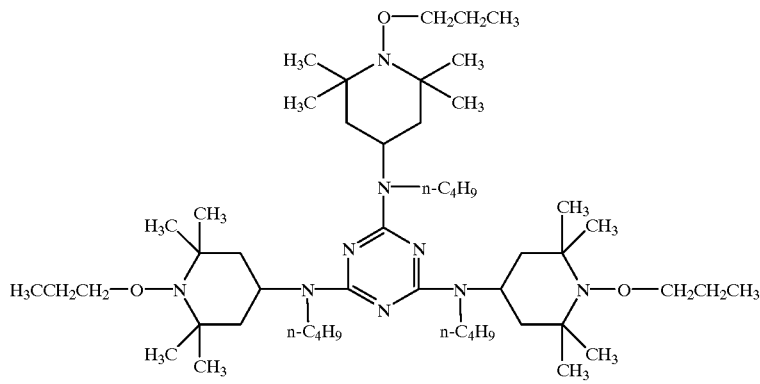

(f') A compound of the formula (1f)

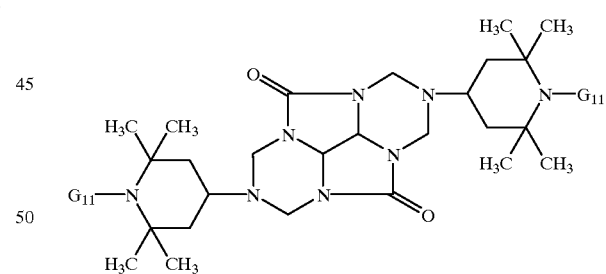

(1f)

wherein $G_{11}$ is as defined under (b').

(g') Oligomeric or polymeric compounds whose recurring structural unit contains a 2,2,6,6-tetraalkylpiperidinyl radical, in particular polyesters, polyethers, polyamides, polyamines, polyurethanes, polyureas, polyaminotriazines, poly(meth)acrylates, poly(meth)acrylamides and copolymers thereof which contain such radicals.

Examples of 2,2,6,6-polyalkylpiperidine compounds from this class are the compounds of the following formulae, where $m_1$ to $m_{14}$ is a number from 2 to about 200, preferably 2 to 100, for example 2 to 50, 2 to 40 or 3 to 40 or 4 to 10.

The meanings of the end groups which saturate the free valences in the oligomeric or polymeric compounds listed below depend on the processes used for the preparation of said compounds. The end groups can also in addition be modified after the synthesis of the compounds.

Examples are compounds of the formula (1g-1)

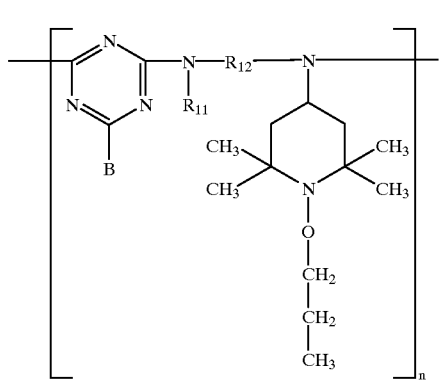

(1g-1)

in which the index n ranges from 1 to 15, being especially from the range 3–9; $R_{12}$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic');

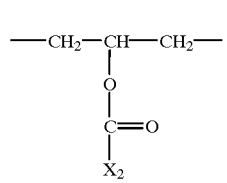

(Ib')

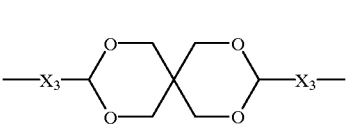

(Ic')

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene; the radicals B are independently of one another Cl, —O$R_{13}$, —N($R_{14}$)($R_{15}$) or a group of the formula (IIId);

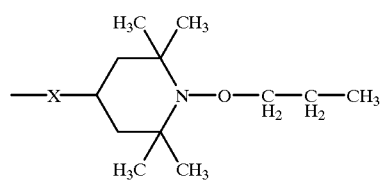

(IIId)

$R_{13}$, $R_{14}$ and $R_{15}$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (Ie');

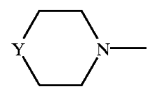

(Ie')

with Y being —O—, —$CH_2$—, —$CH_2CH_2$— or >N—$CH_3$, or —N($R_{14}$)($R_{15}$) is additionally a group of the formula (Ie'); X is —O— or >N—$R_{16}$; $R_{16}$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IIIf),

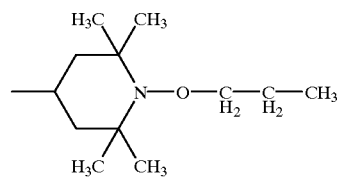

(IIIf)

or $C_2$–$C_4$alkyl which is substituted in the 2, 3 or 4 position by —OH, $C_1$–$C_8$alkoxy, di($C_1$–$C_4$alkyl)amino or a group of the formula (Ie'); $R_{11}$ has one of the definitions given for $R_{16}$.

In these compounds, the end group bonded to the triazine residue can be, for example, a group B or —N($R_{11}$)—$R_{12}$—B, such as chlorine or a group

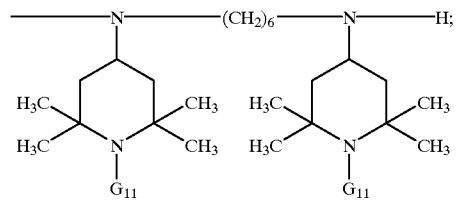

and the end group bonded to the diamino group can be, for example, hydrogen or a di-B-substituted triazinyl group, such as a group

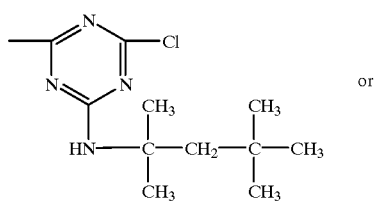

or

-continued

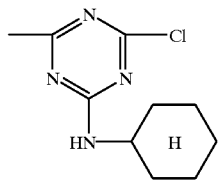

It may be convenient to replace the chlorine attached to the triazine by e.g. —OH or an amino group. Suitable amino groups are typically: pyrrolidin-1-yl, morpholino, —NH$_2$, —N(C$_1$–C$_8$alkyl)$_2$ and —NY'(C$_1$–C$_8$alkyl) wherein Y' is hydrogen or a group of the formula

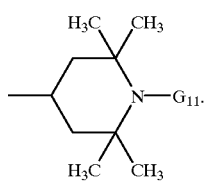

In the above shown oligomeric and polymeric compounds, examples of alkyl are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl and docosyl; examples of cycloalkyl are cyclopentyl, cyclohexyl, cycloheptyl and cyclooctyl; an example of C$_7$–C$_9$phenylalkyl is benzyl; and examples of alkylene are ethylene, propylene, trimethylene, tetramethylene, pentamethylene, 2,2-dimethyltrimethylene, hexamethylene, trimethylhexamethylene, octamethylene and decamethylene.

(h') A compound of the formula (1h)

$$\left[ \begin{array}{c} G-CH_2 \\ G_{11}-N \\ G-CH_2 \end{array} \begin{array}{c} CH_3 \\ \\ CH_3 \end{array} \begin{array}{c} O \\ N-G_{14} \end{array} \right]_{n_6}$$ (1h)

in which n$_6$ is the number 1 or 2, G and G$_{11}$, are as defined under (a'), and G$_{14}$ is as defined under (b').

(i') A compound of the formula (1i)

(1i)

wherein the radicals G$_{39}$, independently of one another, are a group of the formula (1i-1)

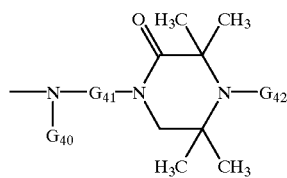

in which G$_{40}$ is C$_1$–C$_{12}$alkyl or C$_2$–C$_{12}$cycloalkyl, G$_{41}$ is C$_2$–C$_{12}$alkylene and G$_{42}$ is hydrogen, C$_1$–C$_8$alkyl, —O, —CH$_2$CN, C$_3$–C$_6$alkenyl, C$_7$–C$_9$phenylalkyl, C$_7$–C$_9$phenylalkyl which is substituted on the phenyl radical by C$_1$–C$_4$alkyl; or C$_1$–C$_8$acyl.

Alkyl is for example C$_1$–C$_4$alkyl, in particular methyl, ethyl, propyl or butyl.

Cycloalkyl is preferably cyclohexyl.

Alkylene is for example ethylene, propylene, trimethylene, tetramethylene, pentamethylene, 2,2-dimethyltrimethylene or hexamethylene.

Alkenyl is preferably allyl.

Phenylalkyl is preferably benzyl.

Acyl is preferably acetyl.

Especially preferred is a compound of the formula IIIb (IIIb)

in which the radicals A are independently of one another —OR$_{13}$, —N(R$_{14}$)(R$_{15}$) or a group of the formula (IIId);

(IIId)

X is —O— or >N—R$_{16}$;

R$_{16}$ is hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IIIf),

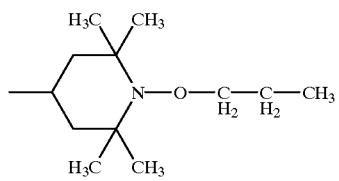

(IIIf)

or $C_2$–$C_4$alkyl which is substituted in the 2, 3 or 4 position by —OH, $C_1$–$C_8$alkoxy, di($C_1$–$C_4$alkyl)amino or a group of the formula (Ie'); $R_{11}$ has one of the definitions given for $R_{16}$; and the radicals B have independently of one another one of the definitions given for A; and where formula (Ie') and all other symbols are as defined above for formula Ia.

The radicals B, $R_{11}$ and $R_{12}$ in the individual recurrent units may be identical or different within the meanings given.

(j') A compound of the formula (2a)

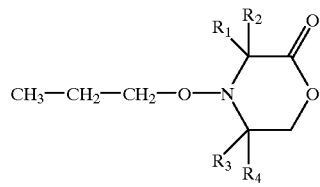

(2a)

in which $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl.

Specific examples for hydrogenated products of present invention include the following compounds:

1-propoxy-2,2,6,6-tetramethyl-4-piperidone, 1-propoxy-2,2,6,6-tetramethyl-4-piperidol, bis(1-propoxy-2,2,6,6-tetramethyl-4-piperidyl)-(3',5'-di-tert.butyl-4'-hydroxybenzyl) butylmalonate, bis(1-propoxy-2,2,6,6-tetramethyl-4-piperidyl)sebacate, bis(1-propoxy-2,2,6,6-tetramethyl-4-piperidyl)succinate, N,N'-bis(1-propoxy-2,2,6,6-tetramethyl-4-piperidyl) hexane-1,6-diamine, N-butyl-1-propoxy-2,2,6,6-tetramethyl-4-piperidinamine, 5-(1-propoxy-2,2,6,6-tetramethyl-4-piperidyl)-2-cyclo-undecyloxazole, 1,6-hexanediyl -N,N'-bis(1-propoxy-2,2,6,6-tetramethyl-4-piperidyl-formamide), 1,5-dioxaspiro(5,5) undecane-3,3-dicarboxylic acid bis(1-propoxy-2,2,6,6-tetramethyl-4-piperidyl) ester, 1,5,8,12-tetrakis(2',4'-bis(1"-propoxy-2",2",6",6"-tetramethyl-4"-piperidyl(butyl)amino)-1',3',5'-triazin-6'-yl)-1,5,8,12-tetraazadodecane, 1,3,5-tris(N-cyclohexyl-N-(1 -propoxy-2,2,6,6-tetramethylpiperazine-3-one-4-yl)amino)-s-triazine, linear or cyclic condensates of N,N'-bis(1-propoxy-2,2,6,6-tetramethyl-4-piperidyl)hexamethylenediamine and 4-tert-octylamino-2,6-dichloro-1,3,5-triazine, tris(1-propoxy-2,2,6,6-tetramethyl-4-piperidyl)nitrilotriacetate, tetrakis-(1-propoxy-2,2,6,6-tetramethyl-4-piperidyl)-1,2,3,4-butane-tetracarboxylate, 1,1'-(1,2-ethanediyl)-bis-(4-propoxy-3,3,5,5-tetramethylpiperazinone), 4-benzoyl-1-propoxy-2,2,6,6-tetramethylpiperidine, 4-stearyloxy-1-propoxy-2,2,6,6-tetramethylpiperidine, 3-n-octyl-8-propoxy-7,7,9,9-tetramethyl-1,3,8-triazaspiro[4,5]decan-2,4-dione, linear or cyclic condensates of N,N'-bis-(1-propoxy-2,2,6,6-tetramethyl-4-piperidyl)hexamethylenediamine and 4-morpholino-2,6-dichloro-1,3,5-triazine, the condensate of 2-chloro-4,6-bis(4-n-butylamino-1-propoxy-2,2,6,6-tetramethylpiperidyl)-1,3,5-triazine and 1,2-bis(3-aminopropylamino)ethane, 8-propoxy-3-dodecyl-7,7,9,9-tetramethyl-1,3,8-triazaspiro[4,5]decane-2,4-dione, 3-dodecyl-1-(1-propoxy-2,2,6,6-tetramethyl-4-piperidyl) pyrrolidin-2,5-dione, a mixture of 4-hexadecyloxy- and 4-stearyloxy-1-propoxy-2,2,6,6-tetramethylpiperidine, a condensation product of N,N'-bis(1-propoxy-2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-1-propoxy-2,2,6,6-tetramethylpiperidine; N-(1-propoxy-2,2,6,6-tetramethyl-4-piperidyl)-n-dodecylsuccinimid, 2-undecyl-8-propoxy-7,7,9,9-tetramethyl-1-oxa-3,8-diaza-4-oxo-spiro [4,5]decane, a reaction product of 8-propoxy-7,7,9,9-tetramethyl-2-cycloundecyl-1-oxa-3,8-diaza-4-oxospiro [4,5]decane and epichlorohydrin, N,N'-bis-formyl-N,N'-bis(1-propoxy-2,2,6,6-tetramethyl-4-piperidyl) hexamethylenediamine, poly[methyl-propyl-3-oxy-4-(1-propoxy-2,2,6,6-tetramethyl-4-piperidyl)]siloxane, reaction product of maleic acid anhydride-α-olefin-copolymer with 1-propoxy-2,2,6,6-tetramethyl-4-aminopiperidine; or the compound R—NH—(CH$_2$)$_3$—N(R)—(CH$_2$)$_2$—N(R)—(CH$_2$)$_3$—NH—R, with R=

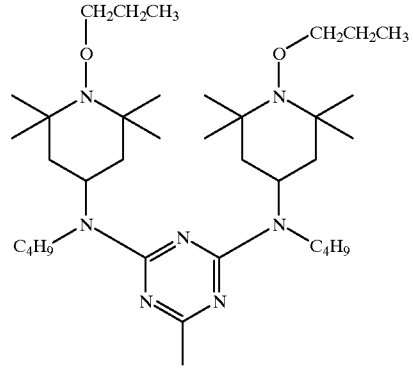

Compounds of the formulae I, III and V, especially IIIa and IIIb can be employed with advantage for stabilizing organic material against the damaging effect of light, oxygen and/or heat, especially for stabilizing synthetic organic polymers or compositions containing them. They are notable for high thermal stability, substrate compatibility and good persistence in the substrate.

Examples of polymers which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Of particular interest is the use of compounds of the formula IIIa as stabilizers in synthetic organic polymers, for example a coating or a bulk polymer or article formed therefrom, especially in thermoplastic polymers and corresponding compositions as well as in coating compositions. Thermoplastic polymers of most importance in present compositions are polyolefines and their copolymers, such as listed above under items 1–3, thermoplastic polyolefin (TPO), thermoplastic polyurethan (TPU), thermoplastic rubber (TPR), polycarbonate, such as in item 19 above, and blends, such as in item 28 above. Of utmost importance are polyethylene (PE), polypropylene (PP), polycarbonate (PC) and polycarbonate blends such as PC/ABS blends, as well as in acid or metal catalyzed coating compositions.

In general the compounds of present invention are added to the material to be stabilized in amounts of from 0.1 to 10%, preferably from 0.01 to 5%, in particular from 0.01 to 2% (based on the material to be stabilized). Particular preference is given to the use of the novel compounds in amounts of from 0.05 to 1.5%, especially from 0.1 to 0.5%. Where compounds of present invention are used as flame retardants, dosages are usually higher, e.g. 0.1 to 25% by weight, mainly 0.1 to 10% by weight of the organic material to be stabilized and protected against inflammation.

Incorporation into the materials can be effected, for example, by mixing in or applying the compounds of the formula I, IIIa, IV, V and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula IIIa into polymers is to add them before, during or directly after the polymerization of the corresponding monomers or prior to crosslinking. In this context the compound of the formula IIIa can be added as it is or else in encapsulated form (for example in waxes, oils or polymers). In the case of addition prior to or during the polymerization, the compounds of the formula IIIa can also act as a regulator of the chain length of the polymers (chain terminator).

The compounds of the formula IIIa can also be added in the form of a masterbatch containing said compound in a concentration, for example, of from 2.5 to 25% by weight to the polymers that are to be stabilized.

The compounds of the formula IIIa can judiciously be incorporated by the following methods:

as emulsion or dispersion (e.g. to latices or emulsion polymers), as a dry mixture during the mixing in of additional components or polymer mixtures, by direct introduction into the processing apparatus (e.g. extruders, internal mixers, etc), as solution or melt.

Novel polymer compositions can be employed in various forms and/or processed to give various products, for example as (to give) films, fibres, tapes, moulding compositions, profiles, or as binders for coating materials, adhesives or putties.

In addition to the compounds of the formula IIIa the novel compositions may as additional component C comprise one or more conventional additives such as, for example, those indicated below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4, 6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, 6-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol. p 1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β(3-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxy-phenylpropionyl) trimethylenediamide, N,N'-bis(3,5-di-tert-butyl-4-hydroxyphenylpropionyl)-hydrazide, N,N'-bis[2-(3-[3,5-ditert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-secbutyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyidiphenylamine, 4-isopropoxy-diphenylamine, N-phenyl-1- naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tertoctylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyidiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxylphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_{\overline{2}}$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tertbutylbenzyl)malonate, 3-n-octyl-7,7,9,9-tetramethyl-1,3,8-triazaspiro[4.5]decan-2, 4-dione, bis(1 -octyloxy-2,2,6,6-tetramethylpiperidyl) sebacate, bis(1 -octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3

-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine, 2,4-bis[N-(1 -cyclohexyloxy-2,2,6,6-tetramethylpiperidine-4-yl)-N-butyl-amino]-6-(2-hydroxyethyl)amino-1,3,5-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5 -triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2-{2-hydroxy-4-[1-octyloxycarbonyl-ethoxy]phenyl}-4,6-bis(4-phenylphenyl)-1,3,5-triazine wherein the octyl moiety is a mixture of different isomers.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl) phosphite (Irgafose®, Ciba-Geigy), tris(nonylphenyl) phosphite,

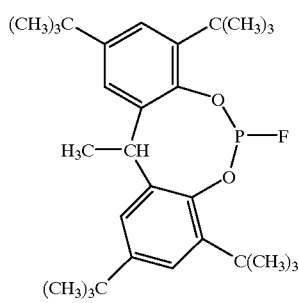

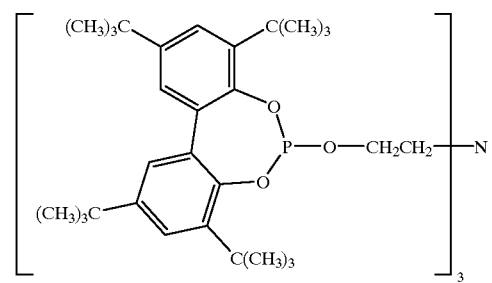

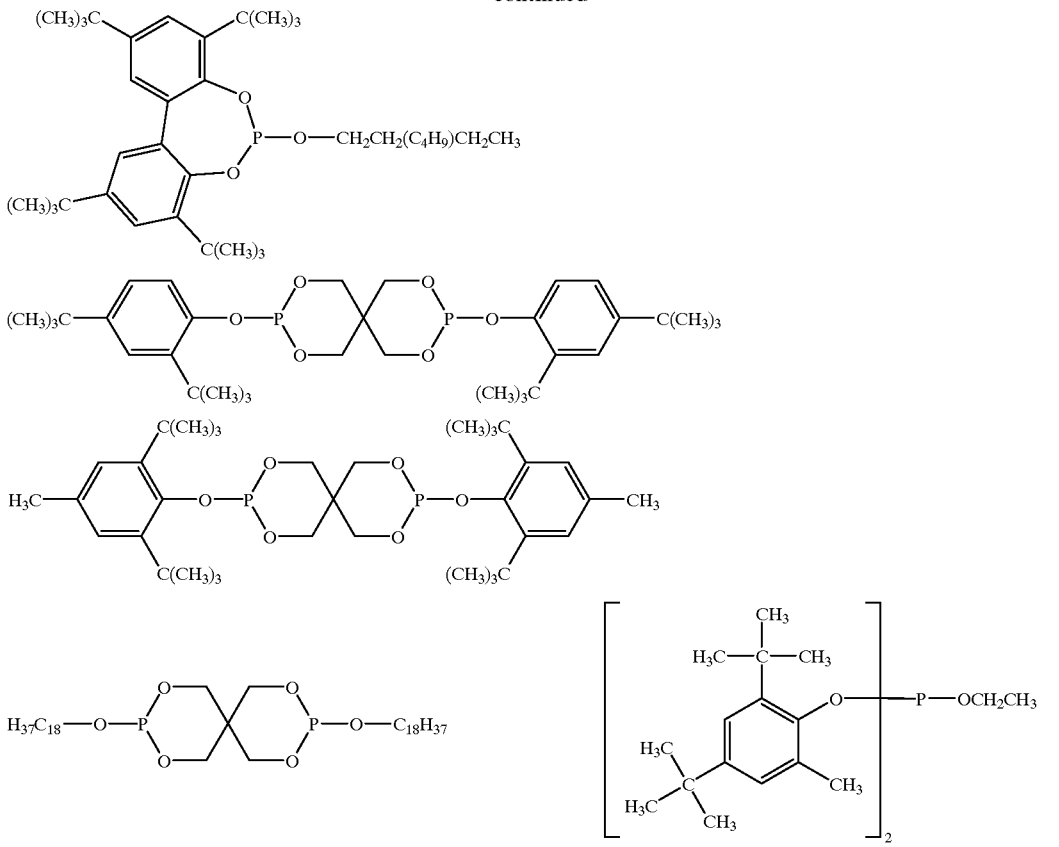

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhy-droxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244, U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tertbutyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The conventional additives are judiciously employed in amounts of 0.1–10% by weight, for example 0.2–5% by weight, based on the material to be stabilized.

Costabilizers optionally to be added to the stabilizer mixture of the invention are preferably further light stabilizers, for instance those of the 2-hydroxyphenyl-benztriazole, 2-hydroxyphenyl-triazine, benzophenone or oxalanilide classes, e.g. as described in EP-A-453396, EP-A-434608, U.S. Pat. No. 5,298,067, WO 94/18278, GB-A-2297091 and WO 96/28431, and/or further hindered amines derived from 2,2,6,6-tetraalkylpiperidine containing at least one group of the formula

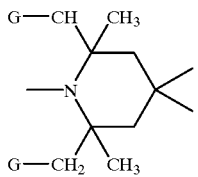

in which G is hydrogen or methyl, especially hydrogen; examples of tetraalkylpiperidine derivatives which can be used as costabilizers with mixtures of the invention are given in EP-A-356 677, pages 3–17, sections a) to f). These sections of this EP-A are regarded as part of the present description.

Likewise of particular interest is the use of the novel mixtures comprising compounds of the formula IIIa as stabilizers for coatings, for example for paints. The invention therefore also relates to those compositions whose component (A) is a film-forming binder for coatings.

The novel coating composition preferably comprises 0.01–10 parts by weight of (B), in particular 0.05–10 parts by weight of (B), especially 0.1–5 parts by weight of (B), per 100 parts by weight of solid binder (A).

Multilayer systems are possible here as well, where the concentration of the novel stabilizer (component (B)) in the outer layer can be relatively high, for example from 1 to 15 parts by weight of (B), in particular 3–10 parts by weight of (B), per 100 parts by weight of solid binder (A).

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder (component (A)) can in principle be any binder which is customary in industry, for example those described in Ullmann's Encyclopedia of Industrial Chemistry, 5th Edition, Vol. A18, pp. 368–426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (A) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. Al 8, p.469, VCH Verlagsgesellschaft, Weinheim 1991.

Preference is given to coating compositions in which component (A) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;

2. two-component polyurethane paints based on hydroxyl-containing acrylate, polyester or polyether resins and aliphatic or aromatic isocyanates, isocyanurates or polyisocyanates;

3. one-component polyurethane paints based on blocked isocyanates, isocyanurates or polyisocyanates which are deblocked during baking, if desired with addition of a melamine resin;

4. one-component polyurethane paints based on a Tris-alkoxycarbonyltriazine crosslinker and a hydroxyl group containing resin such as acrylate, polyester or polyether resins;

5. one-component polyurethane paints based on aliphatic or aromatic urethaneacrylates or polyurethaneacrylates having free amino groups within the urethane strukture and melamine resins or polyether resins, if necessary with curing catalyst;

6. two-component paints based on (poly)ketimines and aliphatic or aromatic isocyanates, isocyanurates or polyisocyanates;

7. two-component paints based on (poly)ketimines and an unsaturated acrylate resin or a polyacetoacetate resin or a methacrylamidoglycolate methyl ester;

8. two-component paints based on carboxyl- or amino-containing polyacrylates and polyepoxides;

9. two-component paints based on acrylate resins containing anhydride groups and on a polyhydroxy or polyamino component;

10. two-component paints based on acrylate-containing anhydrides and polyepoxides;

11. two-component paints based on (poly)oxazolines and acrylate resins containing anhydride groups, or unsaturated acrylate resins, or aliphatic or aromatic isocyanates, isocyanurates or polyisocyanates;

12. two-component paints based on unsaturated polyacrylates and polymalonates;

13. thermoplastic polyacrylate paints based on thermoplastic acrylate resins or externally crosslinking acrylate resins in combination with etherified melamine resins;

14. paint systems based on siloxane-modified or fluorine-modified acrylate resins.

In addition to components (A) and (B), the coating composition according to the invention preferably comprises as component (C) a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A-434608, U.S. Pat. No. 5,198,498, U.S. Pat. No. 5,322,868, U.S. Pat. No. 5,369,140, U.S. Pat. No. 5,298,067, WO-94/18278, EP-A-704437, GB-A-2297091, WO-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines.

Component (C) is preferably used in an amount of 0.05–5 parts by weight per 100 parts by weight of the solid binder.

Apart from components (A), (B) and, if used, (C), the coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. The coatings are preferably cured at 50–150° C., and in the case of powder coatings or coil coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula F according to the invention. The paint is preferably a topcoat for automobiles. The invention furthermore relates to a process for stabilizing a coating based on organic polymers against damage by light, oxygen and/or heat, which comprises mixing with the coating composition a mixture comprising a compound of the formula F, and to the use of mixtures comprising a compound of the formula F in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438–444. The additive of present invention can be used therein e.g. as described e.g. in EP-A-856563, especially page 22, line 21, until page 26, line 29, and literature cited in this reference. The powder coating material may also have the form of a powder-slurry (dispersion of the powder preferably in water).

Examples of resins for powder coatings are:

1. Carboxy- or hydroxy-functionalised polyester resins, based on monomers such as terephthalic acid, isophthalic acid, neopentyl glycol, 2-methyl-1,3-propandiol, tris-1,1,1-(hydroxymethyl)propane etc.

2. Epoxy resins based on bisphenols, such as bisphenol A or Novolac® epoxy resins for thermal or uv-cure with cationic photoinitiators.

3. Hydroxy-, carboxy- or glycidyl-functionalised acrylate polymers and copolymers. Suitable comonomers include styrene, alkyl methacrylates, acrylamide, acrylonitrile etc.

4. Unsaturated polyester resins for uv-cureable powder coatings, typically used in conjunction with multifuntional vinyl ethers or acrylate esters.

Powder coating based on resins with carboxy functionality are typically used together with crosslinking agents of the following classes:

1) polyfunctional epoxy compounds, such as epoxy resins, triglycidylisocyanurate, epoxidised unsaturated fatty acid esters (such as Uranox® resins from DSM), and esters and ethers of glycidol (such as Araldit® PT910 from Ciba Specialty Chemicals).

2) β-hydroxyalkylamides, such as Primid® types XL552 and QM1260 from Ems Chemie. 3) derivatives of melamine, benzoguanimine and glycoluril, such as Powderlink® 1174 from American Cyanamid.

Crosslinking agents for resins of hydroxy functionality include anhydrides and especially blocked diisocyanates and uretdiones, etc.

Powder coatings based on resins with epoxy functionality are typically used together with crosslinking agents such as diacids (such as 1,12-dodecanedioic acid), carboxy-functional polyesters, carboxy-functional copolymers of acrylates and methacrylates, anhydrides (such as the anhydride prepared from 1,12-dodecanedioic acid).

Other additives that can be used together with the compounds of the invention in powder coatings include: degassing agents, flow promoters, tribocharging additives cure catalysts, sensitisers, cationic and free-radical photoinitiators, as well as typical liquid paint additives.

A particular advantage of the compounds of the invention is their low basicity, as basic compounds often catalyse the crosslinking reactions of powder coatings to cause poor flow and degassing, and reduced storage stability. This is particularly useful in formulations of high reactivity, such as the glycidylmethacrylate-functionalised acrylics. Here, the combination of the compounds of the invention together with uv-absorbers, especially of the hydroxyphenyltriazine class, can be used to improve the weatherability without causing catalysis. In other binder systems and with other classes of uv-absorbers, such as those previously mentioned to be of particular use in automotive paints, synergistic effects on the weatherability are also found.

In powder coatings the compounds of the invention can also be used to improve the oxidative stability and reduce yellowing on curing and overbaking. Here not only is the low basicity advantageous, but also the ability of the hindered morpholinones to withstand and prevent yellowing caused by oxides of nitrogen in gas-fired ovens. Use together particularly with phosphite and phosphonite costabilisers, as disclosed in EP-A-816442, and dialkylesters of dithiopropionic acid is particularly beneficial. The compounds of the invention can, where appropriate also be used to stabilise polyester during manufacture as well as at all stages of its subsequent use.

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

Some products of present process are novel compounds.

Present invention therefore also pertains to a compound of the formula I, especially a compound of the formula Ia, wherein $R_5$, $R_6$, $R_7$, $R_8$ and $R_9$, independently of each other, are H, $C_1$–$C_8$alkyl, $C_3$–$C_8$alkenyl, $C_5$–$C_{12}$aryl, an electron withdrawing group, $C_6$–$C_{12}$aryl which is substituted by $C_1$–$C_4$alkyl, $C_1$–$C_4$alkoxy, halogen, and wherein at least one of $R_5$, $R_6$, $R_7$, $R_8$ and $R_9$ is not H. Present invention also pertains to a compound of the formula I, especially a compound of the formula Ia, wherein $R_5$, $R_6$, $R_7$, $R_8$ and $R_9$, independently of each other, are $C_1$–$C_8$alkyl, $C_3$–$C_8$alkenyl, $C_5$–$C_{12}$aryl, an electron withdrawing group, $C_6$–$C_{12}$aryl which is substituted by $C_1$–$C_4$alkyl, $C_1$–$C_4$alkoxy, halogen; and all other symbols are as defined above.

Preferred compounds of the formula I are those of the formula Ia

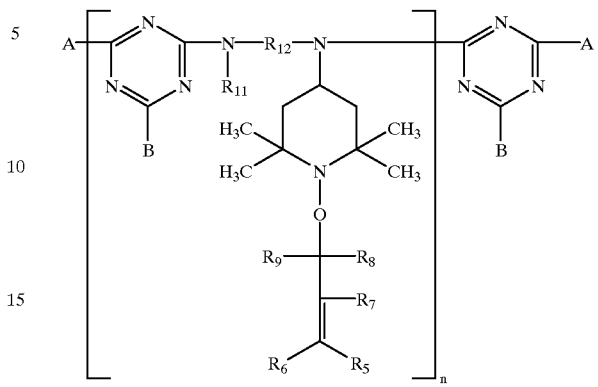

in which the index n ranges from 1 to 15, being especially from the range 3–9;
$R_5$–$R_9$ are as defined for formula I; $R_{12}$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi ($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy) carbonyl or having one of the definitions of $R_{14}$ given below except hydrogen; or $R_{12}$ is a group of the formula (Ib') or (Ic');

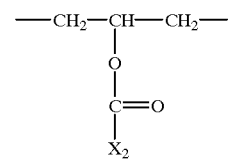

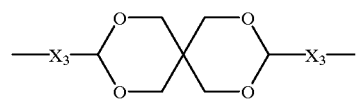

with m being 2 or 3,
$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene; the radicals A are independently of one another —$OR_{13}$, —$N(R_{14})(R_{15})$ or a group of the formula (Id');

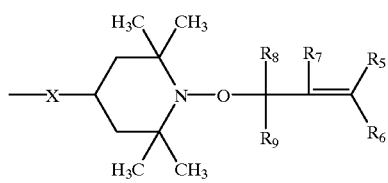

$R_{13}$, $R_{14}$ and $R_{15}$, which are identical or different, are hydrogen, $C_1$–$C_{18}$alkyl, $C_5$–$C_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (Ie');

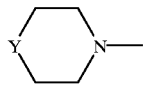

(Ie')

with Y being —O—, —CH$_2$—, —CH$_2$CH$_2$— or >N—CH$_3$, or —N(R$_{14}$)(R$_{15}$) is additionally a group of the formula (Ie'); X is —O— or >N—R$_{16}$; R$_{16}$ is hydrogen, C$_1$–C$_{18}$alkyl, C$_3$–Cl$_8$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (If'),

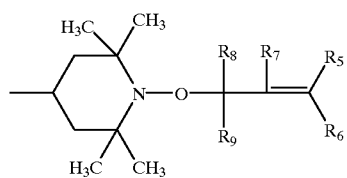

(If')

or C$_2$–C$_4$alkyl which is substituted in the 2, 3 or 4 position by —OH, C$_1$–C$_8$alkoxy, di(C$_1$–C$_4$alkyl)amino or a group of the formula (Ie'); R$_{11}$ has one of the definitions given for R$_{16}$; and the radicals B have independently of one another one of the definitions given for A; and where in the individual recurrent units of the formula (Ia), each of the radicals B, R$_{11}$ and R$_{12}$ may have identical or different meanings.

Further new products of present process correspond to formulae IIIc, IVa and Va

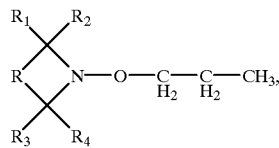

(IIIc)

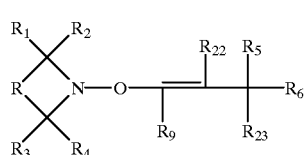

(IVa)

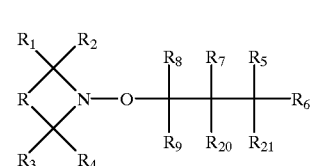

(V)

wherein R is an organic linking group of the formula

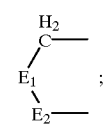

(VI)

E$_2$ is —CO— or —(CH$_2$)$_p$—, where p is 0, 1 or 2; E$_1$ is a carbon atom carrying the two residues R$_{24}$ and R$_{25}$, or is >N—R$_{25}$, or is oxygen, and R$_{24}$ and R$_{25}$ are hydrogen or an organic residue, characterized in that the linking group R in total contains 2–500 carbon atoms and forms, together with the carbon atoms it is directly connected to it and the nitrogen atom, a substituted, 5-, 6 or 7-membered cyclic ring structure; R$_1$, R$_2$, R$_3$ and R$_4$, independently of each other, are C$_1$–C$_8$alkyl or C$_1$–C$_5$hydroxyalkyl, or R$_1$ and R$_2$ together with the carbon atom they are attached to are C$_5$–C$_{12}$cycloalkyl, or R$_3$ and R$_4$ together with the carbon atom they are attached to are C$_5$–C$_{12}$cycloalkyl; R$_5$, R$_6$, R$_7$, R$_8$ and R$_9$, independently of each other, are H, C$_1$–C$_8$alkyl, C$_2$–C$_8$alkenyl, C$_5$–C$_{12}$aryl, C$_1$–C$_4$haloalkyl, an electron withdrawing group, or C$_6$–C$_{12}$aryl which is substituted by a residue selected from C$_1$–C$_4$alkyl, C$_1$–C$_4$alkoxy, halogen; R$_{20}$ and R$_{21}$ are halogen; and R$_{22}$ and R$_{23}$ are hydrogen or together are a chemical bond, with the proviso that R in formula IIIc is not the linking group

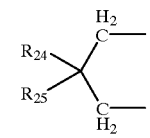

wherein R$_{24}$ and R$_{25}$ together are =O or wherein R$_{24}$ is hydrogen and R$_{25}$ is hydrogen, OH, or alkanoyloxy which is substituted by phenoxy or alkylphenoxy.

When E$_1$ is substituted carbon, E$_2$ mainly is —(CH$_2$)$_p$—, especially CH$_2$; when E$_1$ is oxygen or NR$_{25}$, E$_2$ mainly is carbonyl.

Thus, a compound of formula IIIc, IVa or Va is preferred, wherein R is a divalent C$_7$–C$_{500}$ hydrocarbon or a C$_2$–C$_{500}$ hydrocarbon containing 1–200 hetero atoms selected from nitrogen, oxygen, phosphorus, sulfur, silicon and halogen, and conforms to the structure

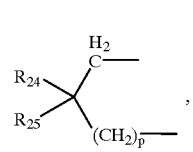

(VIa)

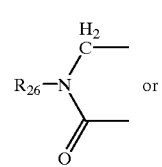

(VIb)

-continued

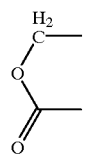
(VIc)

where p is 0, 1 or 2;

$R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; $R_5$ and $R_6$ independently are H or methyl; and $R_7$, $R_8$ and $R_9$ independently are $C_1$–$C_4$haloalkyl, phenyl, vinyl, nitro, CN, $COOR_{10}$, where $R_{10}$ is $C_1$–$C_{12}$alkyl, $C_5$–$C_{12}$cycloalkyl or phenyl; $R_{24}$ and $R_{25}$ independently are hydrogen or an organic residue as defined, and $R_{26}$ is hydrogen or an organic residue forming, together with the remaining structure of formula (VIb) a $C_2$–$C_{500}$hydrocarbon containing 1–200 hetero atoms selected from nitrogen, oxygen, phosphorus, sulfur, silicon and halogen.

Most preferred is a compound of formula IIIc, IVa or Va, wherein $R_5$ and $R_6$ independently are H or methyl; and $R_7$, $R_8$ and $R_9$ independently are $C_1$–$C_4$bromoalkyl, phenyl, CN, $COOR_{10}$, where $R_{10}$ is $C_1$–$C_{12}$alkyl, $C_5$–$C_{12}$cycloalkyl or phenyl; especially wherein $R_5$, $R_6$, $R_7$, $R_8$ and $R_9$ are hydrogen; $R_{20}$ and $R_{21}$ are bromo; and when R conforms to the structure of formula VIa, p is 1 and $R_1$, $R_2$, $R_3$ and $R_4$, independently of each other, are methyl or ethyl; when R conforms to the structure of formula VIb, $R_1$, $R_2$, $R_3$ and $R_4$, independently of each other, are methyl or ethyl; or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl; when R conforms to the structure of formula VIc, $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl.

Special emphasis is given to a compound of the formula IIIc

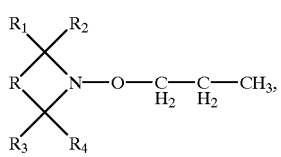
(IIIc)

wherein R is a $C_7$–$C_{500}$hydrocarbon containing 1–200 hetero atoms selected from nitrogen, oxygen, phosphorus, sulfur and halogen, and forming, together with the two carbon and the nitrogen atom, a substituted, 5- or 6-membered cyclic ring structure, and $R_1$, $R_2$, $R_3$ and $R_4$ are as defined above, with the proviso that R does not complete formula IIIc to form a structure of the formula

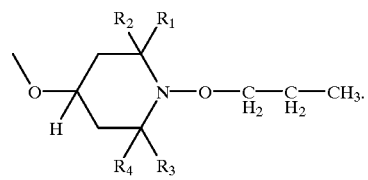

Especially preferred is a compound of the formula IIIc shown above. Thus, the new sterically hindered amine usually corresponds to the formulae (1a), (1b) or (2a) or contains at least one group of the formula (3) or (4)

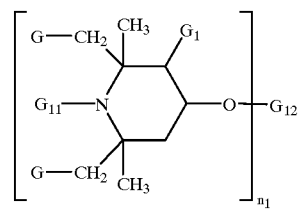
(1a)

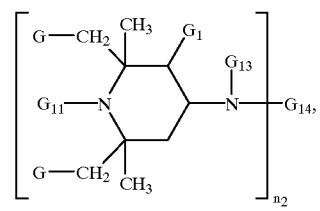
(1b)

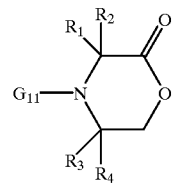
(2a)

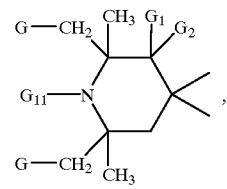
(3)

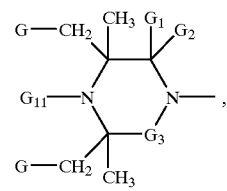
(4)

in which $n_1$ is a number from 1 to 4, G and $G_1$, independently of one another, are hydrogen or methyl, $G_{11}$ is n-propoxy, O—CH=C=CH$_2$, O—CH=CH—CH$_3$ or halogenated n-propoxy, especially n-propoxy, or brominated n-propoxy; G$_{12}$, if n$_1$ is 1, is C$_1$–C$_{18}$alkyl which is uninterrupted or interrupted by one or more oxygen atoms, cyanoethyl, benzoyl, glycidyl, a monovalent radical of an aliphatic, cycloaliphatic, unsaturated or aromatic carboxylic acid, carbamic acid or phosphorus-containing acid or a monovalent silyl radical, preferably a radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms, where each carboxylic acid can be substituted in the aliphatic, cycloaliphatic or aromatic moiety, if present, by 1 to 3 —COOZ$_{12}$ groups, in which Z$_{12}$ is H, C$_1$–C$_{20}$alkyl, C$_3$–C$_{12}$alkenyl, C$_5$–C$_7$cycloalkyl, phenyl or benzyl, G$_{12}$, if n$_1$ is 2, is C$_2$–C$_{12}$alkylene, C$_4$–C$_{12}$alkenylene, xylylene, a divalent radical of an aliphatic, cycloaliphatic, araliphatic or aromatic dicarboxylic acid, dicarbamic acid or phosphorus-containing acid or a divalent silyl radical, preferably a radical of an aliphatic dicarboxylic acid having 2 to 36 carbon atoms, or a cycloaliphatic or aromatic dicarboxylic acid having 8–14 carbon atoms or of an aliphatic, cycloaliphatic or aromatic dicarbamic acid having 8–14 carbon atoms, where each dicarboxylic acid may be substituted in the aliphatic, cycloaliphatic or aromatic moiety by one or two —COOZ$_{12}$ groups, G$_{12}$, if n$_1$ is 3, is a trivalent radical of an aliphatic, cycloaliphatic or aromatic tricarboxylic acid, which may be substituted in the aliphatic, cycloaliphatic or aromatic moiety by —COOZ12, of an aromatic tricarbamic acid or of a phosphorus-containing acid, or is a trivalent silyl radical, and G$_{12}$, if n$_1$ is 4, is a tetravalent radical of an aliphatic, cycloaliphatic or aromatic tetracarboxylic acid; R$_1$, R$_2$, R$_3$ and R$_4$, independently of each other, are C$_1$–C$_8$alkyl or C$_1$–C$_5$hydroxyalkyl, or R$_1$ and R$_2$ together with the carbon atom they are attached to are C$_5$–C$_{12}$cycloalkyl, or R$_3$ and R$_4$ together with the carbon atom they are attached to are C$_5$–C$_{12}$cycloalkyl; G is hydrogen or methyl; G$_1$ and G$_2$, independently of one another, are hydrogen, methyl or together are a substituent =O; and G$_3$ is a direct bond or methylene, open bonds of formulae (3) and (4) are linked to a carbon, nitrogen or oxygen atom of an organic residue as defined above, G$_{13}$ is hydrogen, C$_1$–C$_{12}$alkyl, C$_2$–C$_5$hydroxyalkyl, C$_5$–C$_7$cycloalkyl, C$_7$–C$_8$aralkyl, C$_1$–C$_{18}$alkanoyl, C$_3$–C$_5$alkenoyl, benzoyl or a group of the formula (1b-1)

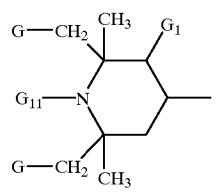
(1b-1)

n$_2$ is the number 1, 2 or 3; and G$_{14}$, if n$_2$ is 1, is hydrogen, C$_1$–C$_{18}$alkyl, C$_3$–C$_8$alkenyl, C$_5$–C$_7$cycloalkyl, C$_1$–C$_4$alkyl which is substituted by a hydroxyl, cyano, alkoxycarbonyl or carbamide group, glycidyl, a group of the formula —CH$_2$—CH(OH)—Z or of the formula —CONH—Z, in which Z is hydrogen, methyl or phenyl; G$_{14}$, if n$_2$ is 2, is C$_2$–C$_{12}$alkylene, C$_6$–C$_{12}$arylene, xylylene, a —CH$_2$–CH(OH)—CH$_2$ group or a —CH$_2$–CH(OH)—CH$_2$—O—D—O— group, in which D is C$_2$–C$_{10}$alkylene, C$_6$–C$_{15}$arylene, C$_6$–C$_{12}$cycloalkylene, or, provided that G$_{13}$ is not alkanoyl, alkenoyl or benzoyl, G$_{14}$ can alternatively be 1-oxo-C$_2$–C$_{12}$alkylene, a divalent radical of an aliphatic, cycloaliphatic or aromatic dicarboxylic acid or dicarbamic acid or alternatively the group —CO—, G$_{14}$, if n$_2$ is 3, is a group

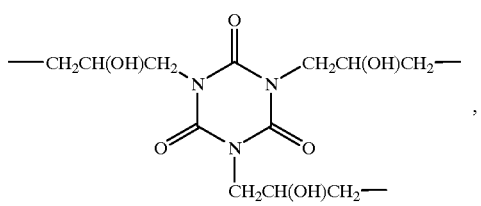

or, if n$_2$ is 1, G$_{13}$ and G$_{14}$ together can be the divalent radical of an aliphatic, cycloaliphatic or aromatic 1,2- or 1,3-dicarboxylic acid.

Preferred new hindered amines of formula IIIc are as described above in sections (b')–(j') and preferences indicated therein. The new compounds of formula IIIc are useful as stabilizers for organic material against degradation by light, oxygen and/or heat. The materials to be stabilized can, for example, be oils, fats, waxes, cosmetics or biocides. Particular interest attaches to use in polymeric materials, as in plastics, rubbers, coating materials, photographic materials or adhesives; examples are organic polymers as described above, and reprographic, especially color photographic material as described, for instance, in GB-A-2319523, DE-A-19750906, page 23, line 20, until page 105, line 32, or in U.S. Pat. No. 5,538,840, column 25, line 60, to column 106, line 31; these parts of U.S. Pat. No. 5,538,840 are incorporated herein by way of reference.

Other preferences are as described above for the compounds of formulae I and III.

The examples below illustrate the invention further. All parts or percentages, in the examples as in the remainder of the description and in the claims, are by weight, unless stated otherwise. Room temperature denotes a temperature in the range 20–30° C., unless stated otherwise. In the examples, the following abbreviations are used:

| | |
|---|---|
| m.p. | melting point or range; |
| Mn | number average of molecular weight (g/mol); |
| Mw | weight average of molecular weight (g/mol); |
| GPC | gel permeation chromatography. |

EXAMPLE 1
Preparation of the starting compound of the formula

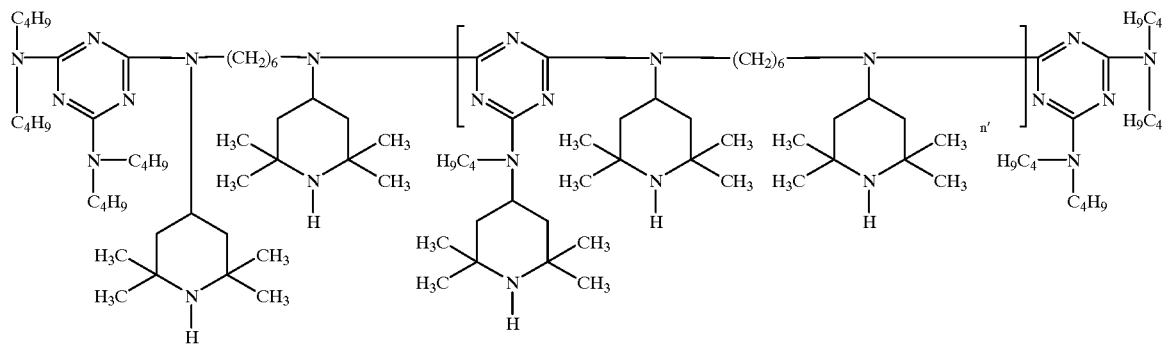

Step 1: A solution of 74.3 g (0.35 moles) of N-(2,2,6,6-tetramethyl-4-piperidinyl)-n-butylamine in 50 ml of water is added slowly at 0° C. to a solution of 64.5 g (0.35 moles) of cyanuric chloride in 500 ml of xylene, keeping the temperature during the addition and for further 1 hour. After 2 hours at room temperature, the mixture is cooled to 0° C. and an aqueous solution of 14.7 g (0.368 moles) of sodium hydroxide in 50 ml of water is added. After ½ hour at 0° C. and for further 2 hours at room temperature, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour and 48.4 g (0.35 moles) of ground potassium carbonate are added and heated to 60° C. for 4 hours.

After washing with water, the organic phase is concentrated under vacuum at 60°–70° C./10 mbar, being 250 ml of xylene recovered. 138.1 g (0.35 moles) of N,N'-bis(2,2,6,6-tetramethyl-4-piperidinyl)-1,6-hexanediamine are added and the mixture is heated to 150° C. for 2 hours, cooled again and added with 14 g (0.35 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 300 ml of xylene, filtered and washed three times with 100 ml of ethylene glycol.

This solution can be used for the isolation of the compound described in Example 6.

Step 2: After concentrating under vacuum at 60° C./10 mbar, 54.4 g (0.147 moles) of 2-chloro-4,6-bis-(dibutylamino)-1,3,5-triazine are added.

The mixture is heated to 140° C. for 3 hours and 20.3 g (0.147 moles) of ground potassium carbonate are added, being the mixture heated to reflux and being the reaction water eliminated off azeotropically.

The mixture is heated to 160° C. for 4 hours, added to further 20.3 g (0.147 moles) of ground potassium carbonate and heated again to 160° C. for 2 hours. After cooling to 60° C., the mixture is diluted with 300 ml of xylene, filtered and concentrated under vacuum at 140° C./1 mbar. A solid is obtained with a melting range of 130–136° C. after drying; Mn (bv GPC): 2830 g/mol.

EXAMPLE 2

Process of present invention; preparation of the compound of the formula

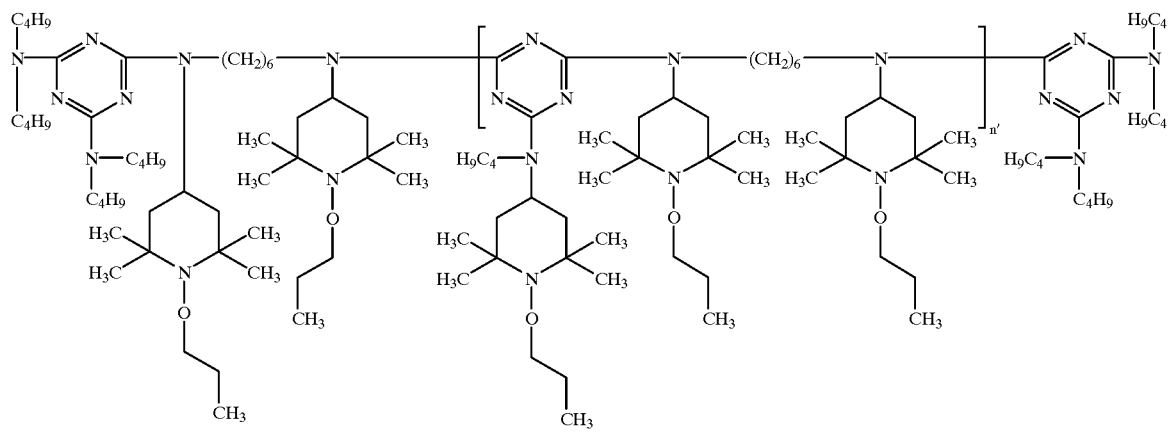

Step 1: In a 1 liter stainless steel autoclave with heating and mechanical stirrer are charged: a solution of 150 g (0.05 mol) of the product of example 1 in 400 ml of xylene, 66.5 g (0.55 mol) of allyl bromide and 114 g (0.825 mol) of potassium carbonate. The mixture is heated to 150° C., left to react for 5 hours and cooled down to 60° C. 300 ml of water are added and the mixture is vigorously stirred. The organic layer is then collected and charged in a 1 liter round bottomed flask equipped with a mechanical stirrer, thermometer and dropping funnel. After cooling to −15° C., 128 g of a solution of 32% by weight of peracetic acid in acetic acid is added during 30 minutes under stirring. The temperature is raised to 0° C. and the reaction mixture is left to react for 4 hours.

A solution of 250 g of $K_2CO_3$ in 500 ml of water is added and kept for 30 minutes at 0° C. with stirring. The organic layer is collected, washed 3 times with 100 ml portions of water, and dried over sodium sulfate.

Step 2: The solution is charged in a 1 l stainless steel autoclave. After addition of 3 g of 5% by weight platinum on carbon, the autoclave is filled with hydrogen of 40 bar and maintained at 70° C. with stirring for a period of 6 hours. Subsequently, the autoclave is cooled to 20° C. and vented. After removing the catalyst by filtration, the solution is concentrated at 140° C. and 1 mbar. The product is obtained as a white solid, m.p. 127°–135° C., Mn (GPC)=3580 g/mol, Mw/Mn=1.33.

EXAMPLE 3

Process of present invention; preparation of the compound of the formula

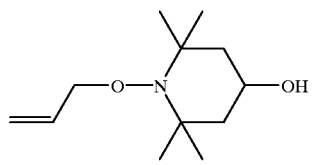

In a round bottomed flask are charged: 20 g of 1allyl-2,2,6,6-tetramethyl-piperidin-4-ol, 40 ml of methanol, 118 g of $H_2O_2$ solution at 35% (v/v). The mixture is heated to 65° C., left to react for 5 hours, concentrated under vacuum until methanol has been distilled off and 40 ml of $CH_2Cl_2$ are added. The mixture is stirred and the organic layer is collected and concentrated. The product is obtained as a pale yellow oil.

$^1$H NMR (300 MHz, CDCl3)/ppm: 5.90–5.80 (m, 1 H); 5.21–4.97 (m, 2 H); 4.24 (m, 2 H); 3.87 (m, 1 H); 1.75 (m, 2 H); 1.42 ( m, 2 H); 1.15 (s, 3 H); 1.11 (s, 3 H).

EXAMPLE 4a

Preparation of the compound of the formula

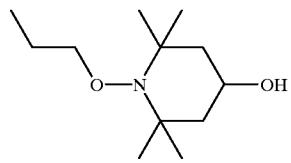

In a stainless steel autoclave are charged : 20 g of the product of example 3, 0.2 g of nickel raney and 100 ml of toluene; the autoclave is filled with hydrogen of 8 bar and maintained at 25° C. under stirring for a period of 8 hours. Subsequently the autoclave is vented , the catalyst is removed by filtration and the mixture is concentrated under vacuum. The product is obtained as a white solid.

$^1$H NMR (300 MHz, CDCl3)/ppm: 3.95 (m,1 H); 3.66 (t, 2 H); 1.57 (m, 4 H); 1.22 (m, 2 H); 1.13 ( s, 12 H); 0.89 (t, 3 H).

EXAMPLE 4b

Preparation of the compound of the formula

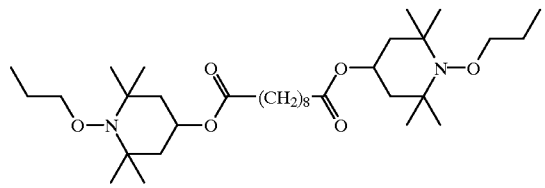

In a round bottomed flask are charged: 20 g of product of example 4a), 10.6 g of methyl sebacate, 100 ml of xylene and 0.25 g of di-butyl-tin-oxide. The mixture is heated to 145° C., left to react for 6 hours with stirring, cooled down and concentrated under vacuum, yielding the above product as an oil.

$^1$H NMR (300 MHz, CDCl3)/ppm: 4.95 (m, 2 H); 3.66 (t, 4 H); 2.21 (t, 4 H); 1.77 (m, 4 H); 1.63–1.42 (m, 12 H); 1.28–1.18 (m, 36 H); 0.90 (t, 6 H).

Other analytical data:

| HPLC assay: | 80% | | |
|---|---|---|---|
| Elemental analysis: | | | |
| | C | measured 67.6% | calculated 68.4% |
| | H | measured 10.6% | calculated 10.8% |
| | N | measured 4.7% | calculated 4.7% |

EXAMPLE 5

Process of present invention; preparation of the compound of the formula

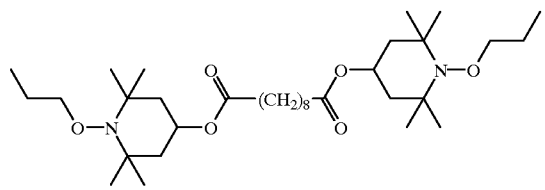

In a stainless steel autoclave are charged 20 g of sebacic acid bis-(2,2,6,6-tetramethylpiperidin-4yl) ester (commercial name: Tinuvin® 770), 24 g of allyl bromide, 6 g of potassium carbonate and 100 ml of toluene; the mixture is heated to 120° C., left to react for 5 hours with stirring, cooled down and filtered to remove the salts. The excess of allyl bromide is removed by distillation.

The solution is charged in a round bottomed flask and 8 g of metachloroperbenzoic acid dissolved in 50 ml of toluene are added over a period time of 30 minutes keeping the temperature below 25° C.

Then a solution of 13 g of potassium carbonate in 100 ml of water is added to the reaction mixture and it is left under stirring for 30 minutes. The organic layer is collected and washed with a potassium carbonate solution prepared as described above. The organic layer is then dried over sodium sulfate and charged in a stainless steel autoclave. After addition of 1 g of 5% by weight platinum on carbon, the autoclave is filled with hydrogen of 8 bar and maintained at 25° C. with stirring for 4 hours. After removing the catalyst by filtration, the solution is concentrated under vacuum. The product is obtained as a pale yellow oil;

$^1$H NMR (300 MHz, CDCl3)/ppm: 4.95 (m, 2H); 3.66 (t, 4H); 2.21 (t, 4H); 1.77 (m, 4H); 1.63–1.42 (m, 12 H); 1.28–1.18 ( m, 36 H); 0.90 (t, 6 H).

Other analytical data:

| HPLC assay: | 78% | | |
|---|---|---|---|
| Elemental analysis: | | | |
| | C | measured 67.2% | calculated 68.4% |
| | H | measured 10.3% | calculated 10.8% |
| | N | measured 4.6% | calculated 4.7% |

EXAMPLE 6

Intermediate of the formula

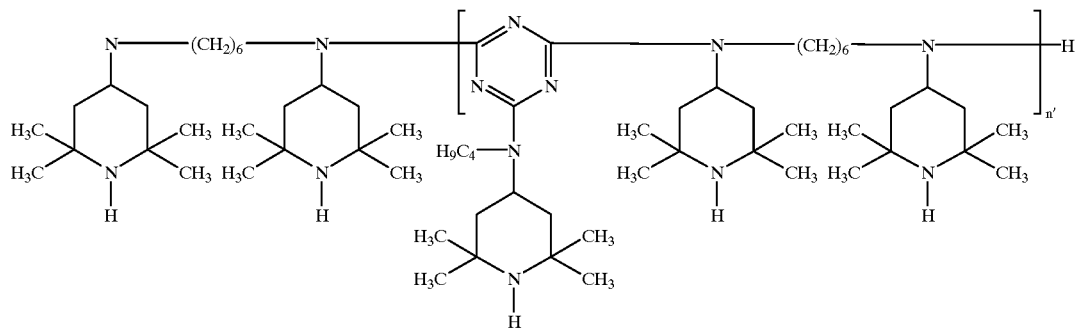

The preparation of the current compound follows the procedure described in Example 1 up to Step 1. The solution obtained from step 1 is then concentrated at 140°C. and 1 mbar and it yields a solid, mp 138–143° C., with an average Mn (by GPC) of 2555 g/mol.

EXAMPLE 7

To a solution of 150 g of the product of example 6 in 400 ml of xylene are added 66.5 g of allyl bromide and 114 g of potassium carbonate. The mixture is heated to 150° C., left to react for 5 hours and cooled down to 60° C. 300 ml of water are added and the mixture is vigorously stirred. The organic layer is then collected, cooled to −15° C. and 128 g of a solution of 32% by weight of peracetic acid in acetic acid is added during 30 minutes under stirring. The temperature is raised to 0° C. and the reaction mixture is left to react for 4 hours. A solution of 250 g of $K_2CO_3$ in 500 ml of water is added while stirring and left to react for 30 minutes at 0° C. The organic layer is collected, washed 3 times with 100 ml portions of water, and dried over sodium sulfate. The solution is charged in a 1 l stainless steel autoclave. After addition of 3 g of 5% by weight platinum on carbon, the autoclave is filled with hydrogen of 40 bar and maintained at 70° C. with stirring for a period of 6 hours. Subsequently, the autoclave is cooled to 20° C. and vented. After removing the catalyst by filtration, the solution is concentrated at 140° C. and 1 mbar. The product is obtained as a white solid, m.p. 125–135° C., Mn (GPC)=2979 g/mol.

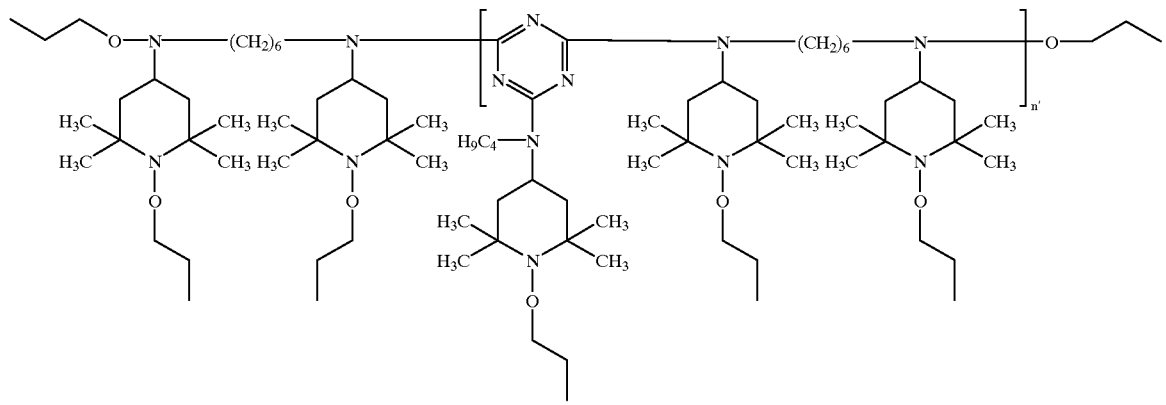

EXAMPLE 8

Compound of the formula

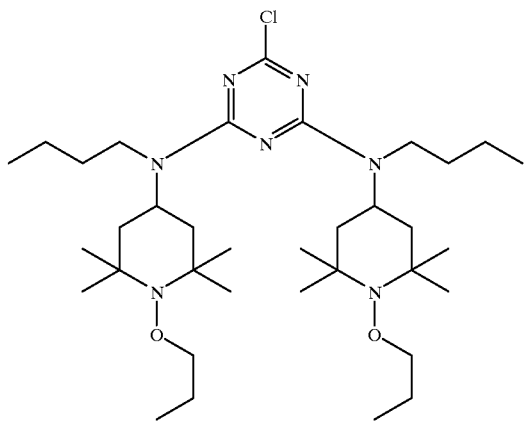

To a solution of 93 g of 2-chloro-4,6-bis-(N-n-butyl-N-(2,2,6,6-tetramethylpiperidin-4-yl))-1,3,5-triazine in 300 ml of toluene are added 42 g of allyl bromide and 71.7 g of potassium carbonate. The mixture is heated to 150° C., left to react for 10 hours, cooled down to 60° C. and 300 ml of water are added while stirring. The organic layer is then collected and cooled to −5° C., 64 g of a solution of 39% by weight of peracetic acid in acetic acid is added during 30 minutes under stirring. The temperature is raised to 0C and the reaction mixture is left to react for 2 hours.

A solution of 90 g of sodium carbonate in 500 ml of water is added and kept for 30 minutes at 0° C. with stirring. The organic layer is collected and dried over sodium sulfate. The solution is charged in a 1 l stainless steel autoclave. After addition of 3 g of 5% by weight platinum on carbon, the autoclave is filled with hydrogen of 40 bar and maintained at 70° C. with stirring for a period of 6 hours. Subsequently, the autoclave is cooled to 20° C. and vented. After removing the catalyst by filtration, the solution is concentrated at 140° C. and 1 mbar. The product is obtained as a white solid.

1 H NMR (300 MHz, CDCl3)/ppm: 4.97 (m, 2 H) ; 3.67 (t, 4 H) ; 3.29 (m, 4 H); 1.80–1.30 (m, 20 H); 1.31–1.08 (m, 28 H); 0.92–0.80 ( m, 12 H).

EXAMPLE 9

Compound of the formula

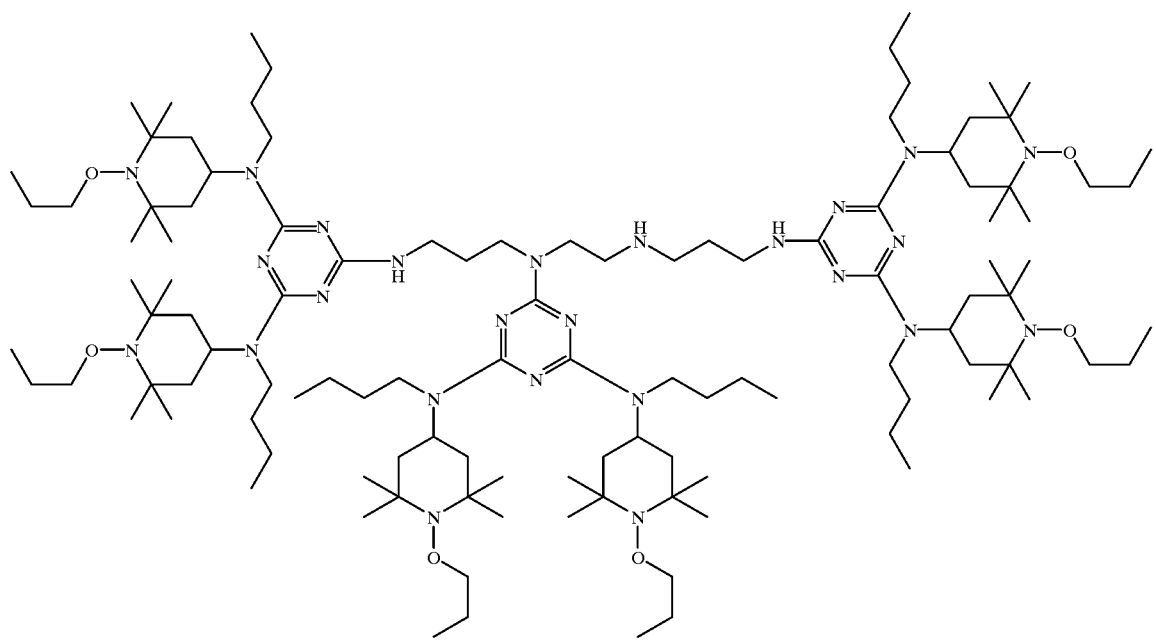

A mixture composed of 64.5 g of the compound described in the example 8, 200 ml of xylene, 20.4 g of potassium carbonate and 4.6 g of N-1-[2-(3-Amino-propylamino)-ethyl]-propane-1,3-diamine is heated up to 140° C. for 10 hours, cooled down to 20° C. and washed with 200 ml of water. The collected organic layer is concentrated at 140° C. and 1 mbar. The solid obtained has a m.p. in the range of 115–120°C.

EXAMPLE 10
Compound of the formula

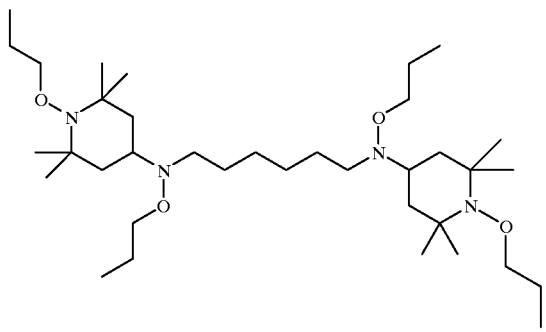

To a solution of 30 g of N,N'-bis(2,2,6,6-tetramethyl-4-piperidinyl)-1,6-hexanediamine in 240 ml of toluene are added 50 g of allyl bromide and 63 g of potassium carbonate. The resulting mixture is heated up to 150° C. and left to react for 6 hours, cooled down to 20° C., filtered and the volume of the solution is reduced at 100 ml by solvent evaporation at 110° C. and 1 mbar of vacuum. To the concentrate solution are added 150 ml of toluene, after cooling down to −10° C. a solution of 82 g of m-chloro perbenzoic acid in 200 ml of toluene is added over one hour under stirring. After heating the mixture up to 0° C., a solution of 100 g of potassium carbonate in 300 ml of water is added under stirring and left to reach 20° C.

The organic layer is collected, dried over sodium sulfate and hydrogenated with 40 bar of hydrogen with 2 g of 5% platinum over carbon at 70° C. for 8 hours. The catalyst is recovered by filtration and the solution is concentrated at 110° C. under 1 mbar.

1 H NMR (300 MHz, CDCl3)/ppm: 3.75 (t, 4 H) ; 3.54 (t, 4 H); 2.82 (m, 2 H); 2.63 (t, 4H); 1.78–1.45 (m, 20 H) ; 1.42–1.23 ( m, 4 H); 1.16 (s, 12 H); 1.10 (s, 12 H), 0.89 (m, 6 H).

EXAMPLE 11
Compound of the formula

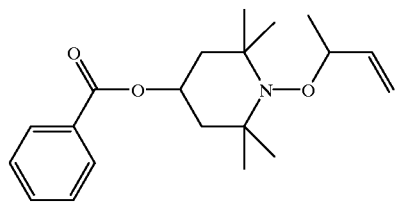

To a solution of 90 g of benzoic acid 1-but-2-enyl-2,2,6,6-tetramethyl-piperidin-4-yl ester in 200 ml of toluene, are added 70 g of 4-Bromo-2-butene and 100 g of potassium carbonate. The mixture is heated to 140° C., left to react for 10 hours under stirring, cooled down to 20° C., poured in 200 ml of water and stirred. The organic layer is then collected, concentrated by removing 100 ml solvent at 110° C. at 20 mbar, then added with 100 ml of fresh toluene. The resulting solution is cooled down to −150° C. and a solution of 100 g of m-chloro-perbenzoic acid in 200 ml of toluene is added during 30 minutes under stirring. The mixture is left to react for 2 hours at 0° C. then a solution of 40 g of potassium carbonate in 300 ml of water is added under stirring. The organic layer is collected and the solvent evaporated under vacuum. The product obtained is a pale yellow liquid.

1 H NMR (300 MHz, CDCl3)/ppm: 7.99 (d, 2 H); 7.49 (m, 1 H) ; 7.37 (m, 2 H); 5.85 (m, 1 H); 5.26 (m,1 H); 5.06–5.00 ( m, 2 H); 4.28 (m, 1 H); 1.94 (m, 2 H) ;1.71 (m, 2 H); 1.25–1.17 (m, 15 H).

EXAMPLE 12
Compound of the formula

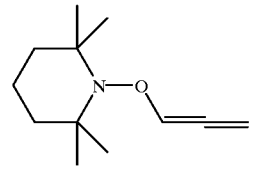

To a solution of 52 g of 2,2,6,6, tetramethylpiperidine in 250 ml of hexane are added 102 g of potassium carbonate and 135 g of propargyl bromide. The mixture is heated to 140° C., left to react for 10 hours under stirring, cooled down to 20° C., poured in 300 ml of water and stirred. The organic layer is then collected, dried over sodium sulphate, and distilled under vacuum collecting the fraction at 64° C. and 10 mmHg which is then dissolved in 250 ml of dichloromethane and cooled to −15° C. To the resulting solution is added a solution of 100 g of m-chloro-perbenzoic acid in 200 ml of hexane in 30 minutes while stirring. The mixture is left to react for 2 hours at 0° C. and a solution of 40 g of potassium carbonate in 300 ml of water is added while stirring. The organic layer is collected, dried over sodium sulfate and the solvent evaporated under vacuum. The product obtained is a pale yellow liquid.

1 H NMR (300 MHz, CDCl3)/ppm: 6.82 (t, 1 H); 5.49 (d, 2 H) ; 1.52 (s, 6 H); 1.13 (s, 12 H).

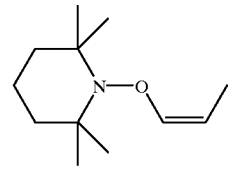

EXAMPLE 13
Compound of the formula
A mixture of 16 g of the compound described in the example 11, 500 ml of ethanol and 0.9 g of Lindlar catalyst is charged in an autoclave. The autoclave is filled with 10 bar of hydrogen and maintained at 40° C. under stirring for a period of 6 hours, then it is cooled to 20° C. and vented. After removing the catalyst by filtration, the solution is concentrated under vacuum. The resulting product is obtained as a pale yellow liquid.

1 H NMR (300 MHz, CDCl3)/ppm: 6.29 (d, 1 H); 4.01 (m, 1 H); 1.57 (d, 3 H); 1.45 (m, 6 H); 1.12 (s, 12 H).

EXAMPLE 14

Compound of the formula

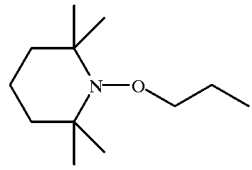

A mixture of 38 g of the compound described in the example 11, 300 ml of toluene and 1 g of platinum supported on carbon at 5% by weight is charged in an autoclave. The autoclave is filled with 30 bar of hydrogen and maintained at 40° C. under stirring for a period of 6 hours, then it is cooled to 20° C. and vented. After removing the catalyst by filtration, the solvent is removed by vacuum concentration at 110° C. and 35 mbar. The resulting product is obtained as a pale yellow liquid.

1 H NMR (300 MHz, CDCl3)/ppm: 3.69 (t, 2 H); 1.45 (m, 8 H); 1.15 (s, 12 H) ; 0.92 (t, 3 H).

EXAMPLE 15

Compound of the formula

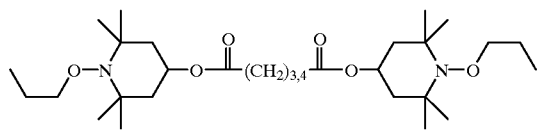

207 g of 4-hydroxy-2,2,6,6-tetramethylpiperidine, 100 g of DBE-2° (a mixture of 75% of glutaric acid dimethyl ester and 25% of adipic acid dimethyl ester, from DuPont-USA) are dissolved in 500 ml of toluene, added with 2 g of lithium amide and heated and maintained to reflux for 6 hours, while the methanol formed during the reaction is distilled off by azeotropation. The mixture is then cooled to 20° C., washed with water, dried over sodium sulfate. The resulting solution is then reacted with allyl bromide, sodium carbonate, peracetic acid, hydrogen and 5% by weight platinum on carbon, following the same procedure and the same stoichiometric ratios described for the preparation of the compound in example 5. The product is obtained as a pale yellow oil.

1 H NMR (300 MHz, CDCl3)/ppm: 4.95 (m, 2 H); 3.63 (t, 4 H); 2.24 (m, 2 H); 1.86–1.71 (m, 4 H–6 H); 1.57–1.44 (m, 8 H); 1.15 (m, 28 H); 0.89 (m, 6 H).

EXAMPLE 16

Compound of the formula

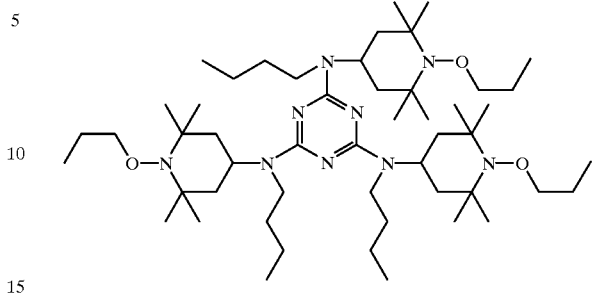

Step 1: To a solution of 64 g of 2,4,6-tris-(N-n-butyl-N-(2,2,6,6-tetramethylpiperidin-4-yl))-1,3,5-triazine in 300 ml of toluene are added 48 g of allyl bromide and 55.8 g of potassium carbonate. The mixture is heated to 150° C., left to react for 5 hours, cooled down to 60° C. and 300 ml of water are added while stirring. The organic layer is then collected, concentrated by removing 100 ml of solvent at 110° C. at 20 mbar, added with 400 ml of fresh toluene, cooled to −5° C. and 57 g of a solution of 39% by weight of peracetic acid in acetic acid is added during 30 minutes under stirring. The temperature is raised to 0° C. and the reaction mixture is left to react for 2 hours.

A solution of 80 g of sodium carbonate in 500 ml of water is added and kept for 30 minutes at 0° C. with stirring. The organic layer is collected and dried over sodium sulfate.

Step 2: The solution is charged in a 1 l stainless steel autoclave. After addition of 2 g platinum supported on carbon at 5% by weight, the autoclave is filled with hydrogen of 40 bar and maintained at 70° C. with stirring for a period of 6 hours, then cooled to 20° C. and vented. After removing the catalyst by filtration, the solution is concentrated at 140° C. and 1 mbar. The product is obtained as a white solid, m.p. 92–100° C.

EXAMPLE 17

Compound of the formula

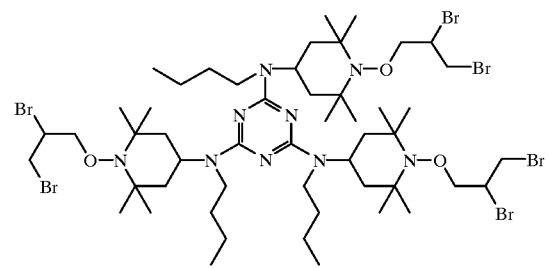

The solution obtained in step 1 of example 14 is added with 43 g of bromine in 30 minutes while stirring at 25° C. in the dark. The mixture is left to react for 6 hours at 25° C., washed with a solution of 54 g of potassium carbonate in 500 ml of water, collected, dried with sodium sulfate and concentrated at 100° C. under reduced pressure (10 mbar). The obtained pale pink solid has a melting point 106–110° C.

EXAMPLE 18

Compound of the formula

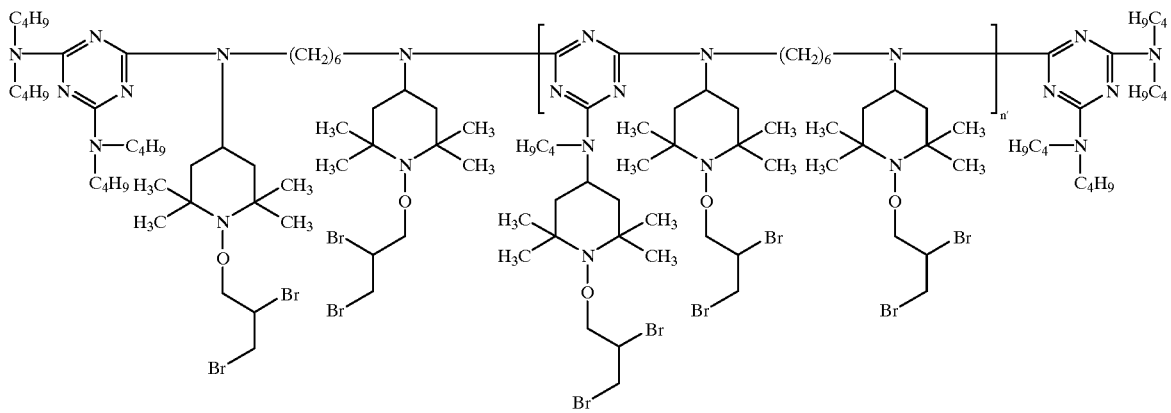

To the solution obtained in step 1 of example 2, 88 g of bromine is added during 30 minutes while stirring at 25° C. in the dark. The mixture is left to react for 6 hours at 25° C., washed with a solution of 108 g of potassium carbonate in 1000 ml of water, collected, dried with sodium sulfate and concentrated at 120° C. under reduced pressure (10 mbar). The obtained pale yellow solid has a melting point higher than 250° C. (decomposition).

Bromine content: 32.1% by weight; Mn (by GPC): 2862.

Application Examples

EXAMPLE 20

LIGHT STABILIZING ACTION IN PP TAPES 1 g of each compound of the list reported below and, 1 g of tris(2,4-di-ter-butylphenyl) phosphite, 0.5 g of pentaerythritol tetrakis (3-(3,5-di-tert-butyl-4hydroxyphenyl) propionate), 1 g of calcium stearate are mixed in a turbomixer with 1000 g of polypropylene powder having a melt index of 2.1 gl 10 minutes (measured at 230° C. and 2.16 Kg) and already containing 1 g of tris(2,4-di-ter-butylphenyl phosphite) and 10.5 g of pentaerythritol tetrakis (3-(3,5-di-tert-butyl-4- hydroxyphenyl)propionate).

The mixture is extruded at 200–220° C. to give polymer granules which are subsequently converted to stretched tapes of 50 microns thickness and 2.5 mm width, using a semi industrial type of apparatus (Leonard-Sumirago(VA)-Italy) and working under the following conditions:

Extruder temperature: 210–230° C.

Head temperature: 240–260° C.

Stretch ratio: 1:6

The tapes thus prepared are mounted on a white card and exposed in Weather-O-Meter 65 WR (ASTM G26-96D 2565-85) with a black panel temperature of 63° C.

The residual tensile strength is measured, by means of a constant velocity tensometer, on a sample taken after various light exposure times; from this, the exposure time (in hours) required to halve the initial tensile strength (T50) is calculated.

For the purpose of comparison, tapes prepared under the same conditions as indicated above, but without the addition of the stabilisers of the present invention, are exposed.

The results obtained are shown in the table below.

| Compound of the Invention | T50 (hours) |
|---|---|
| none | 340 |
| compound of example 5 | 3040 |

EXAMPLE 21

LIGHT STABILIZING ACTION IN LDPE FILMS

Each compound of the list reported below is mixed via master batch with LDPE pellets (Riblene FF 29, supplied by Enichem, Milano, Italy), characterised by a density of 0.921 g/cm$^3$ and a melt flow index (190° C./2.16 Kg) of 0.60 g/10 minutes, in a slow mixer. The master batch had previously been prepared by extruding powdered LDPE and 10% by weight of the compounds of the list reported below.

The mixture is blow extruded at 210° C. and films of 150 microns thickness are obtained.

Films are mounted on a white cardboard in metal frames and exposed in Atlas Ci 65 Xenon Arc Weather-O-meter, at 63° C. black panel temperature, continues dry cycle, according to ASTM G 26–96.

During the exposure, the performance is periodically evaluated measuring the carbonyl increment (iCO; increase of carbonyl concentration) by means of a FT-IR spectrophotometer and testing the samples for embrittlement. For some samples, the residual tensile strength is measured by means of a constant velocity tensometer, on a sample taken after various light exposure times; from this, the exposure time (in hours) required to halve the initial tensile strength (T50) is calculated.

Results are compiled in the following table; a low increase of carbonyl concentration and a high T50 time indicate good stabilisation.

TABLE

Increase of carbonyl concentration (iCO)
after 4760 hours exposure and T50

| Compound | T50/hours | iCO |
|---|---|---|
| 0.2% of example 2 | >7050 | 0.08 |
| without stabiliser | 660 | embrittled after 1560 h |

EXAMPLE 22

LIGHT STABILIZING ACTION IN LDPE FILMS TREATED WITH BORDEAUX MIXTURE

Each compound of the list reported below is mixed via master batch with LDPE pellets (Riblene FF 29, supplied by Enichem, Milano, Italy), characterised by a density of 0.921 g/cm$^3$ and a melt flow index (190° C./2.16 Kg) of 0.60 g/10 minutes, in a slow mixer.

The master batch had previously been prepared by extruding powdered LDPE and 10% by weight of the compound of the list reported below.

The mixture is blow extruded at 210° C. and films of 150 microns thickness are obtained.

Films for pesticide treatment are kept 24 hours in a suspension of Bordeaux mixture (widely used pesticide based on copper sufate) and water (10 g of mixture in 1 liter of water).

Treated films are put into quartz tubes and are exposed in Atlas Ci 65 Xenon Arc Weather-O-meter, at 63° C. black panel temperature, continuos dry cycle, according to ASTM G 26-96.

During the exposure, the performance is periodically evaluated measuring the carbonyl increment (increase of carbonyl concentration; iCO) by means of a FT-IR spectrophotometer. Results are compiled in the following table.

TABLE

Increase of carbonyl concentration (iCO)
after indicated hours of weathering

| Compound | iCO after 0 h |
|---|---|
| 0.15% of example 2 | 0 |
| without stabiliser | 0 |

EXAMPLE 23

LIGHT STABILIZING ACTION IN LDPE FILMS TREATED WITH VAPAM

Each compound of the list reported below is mixed via master batch with LDPE pellets (Riblene FF 29, supplied by Enichem, Milano, Italy), characterised by a density of 0.921 g/cm$^3$ and a melt flow index (190° C./2.16 Kg) of 0.60 g/10 minutes, in a slow mixer.

The master batch had previously been prepared by extruding powdered LDPE and 10% by weight of the compound of the list reported below.

The mixture is blow extruded at 210° C. and films of 150 microns thickness are obtained.

Films for pesticide treatment are kept inside a dryer for 20 days at 30° C., in presence of the vapours emitted by 2 lt of an aqueous solution containing 50% of VAPAM (Baslini S.p.A., Treviglio/BG, Italy), which, in turn, in an aqueous solution of 382 g per litre of metam-sodium, having the formula CH$_3$—NH—CS—SNa.

Treated films are put into quartz tubes and are exposed in Atlas Ci 65 Xenon Arc Weather-O-meter, at 63° C. black panel temperature, continuos dry cycle, according to ASTM G 26-96.

During the exposure, the performance is periodically evaluated measuring the carbonyl increment by means of a FT-IR spectrophotometer and testing the samples for embrittlement. Results are compiled in the following table; a low increase of carbonyl concentration indicates good stabilisation.

TABLE

Increase of carbonyl concentration (iCO) after 1000 hours exposure

| Compound | Concentration | iCO |
|---|---|---|
| example 2 | 0.2% | 0.38 |
| without stabiliser | 0 | embritteled |

EXAMPLE 24

LIGHT STABILIZING ACTION IN GREENHOUSE FILMS

Each compound of the list reported below is mixed via master batch with LDPE pellets (Riblene FF 29, supplied by Enichem, Milano, Italy), characterised by a density of 0.921 g/cm$^3$ and a melt flow index (19° C./2.16 Kg) of 0.60 g/10 minutes, in a slow mixer.

The master batch had previously been prepared by extruding powdered LDPE and 10% by weight of the sterically hindered hydroxylamine ether of present invention (compound A) and the relevant concentrations of component B (=oxo and or hydroxyl group containing metal costabiliser) and C (further costabiliser; salt of carboxylic acid).

The mixture is blow extruded at 210° C. and films of 150 microns thickness are obtained. The films are exposed on the south face roof of a greenhouse in Pontecchio Marconi (Bologna-Italy). The following pesticide are applied in the greenhouse:

VAPAM (Baslini S.p.A., Treviglio/BG, Italy), which, in turn, in an aqueous solution of 382 g per liter of metam-sodium, having the formula CH$_3$—NH—CS—SNa; SESMETRIN (Bimex SpA, Isola/VI, Italy), which is a 23.75% (% w/w) aqueous solution of permethrin having the formula

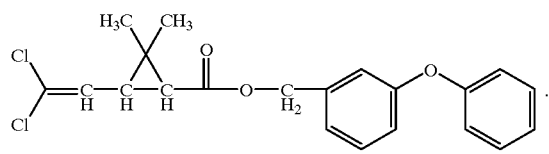

The greenhouse is treated with a solution of 4 liters of VAPAM in 10 liters of water every 6 months, and with SESMETRIN (5 g in 5 liters of water) every month.

During the exposure, the performance is periodically evaluated measuring the carbonyl increment by means of a FT-IR spectrophotometer. The exposure is measured in kilolangley (Klys; energy per unit area); 1100 Klys corresponds to 1 year of exposure.

| Compound A | Component B | Ca-Stearate | iCO after |
|---|---|---|---|
| 0, 4% of example 2 | 0.2% ZnO | 0.2 | |
| 0, 4% of example 2 | 0 | 0 | |
| none | 0 | 0 | |

EXAMPLE 25
Wood Coating a) Impregnation:

The substrate (pine) is impregnated using a a commercially available impregnation ("Xylamon® Incolore" solids content of 5,2% from Sepam).

The impregnation is applied by brush (1 application) and dried for 24 hours at room temperature.

b) Top Coat:

A top coat is prepared from:

73.8 parts of an Alkyd Resin (Jagol PS 21 ®, E. Jäger KG), 0.52 parts of antiskinning agent (Exkin 2®, Servo Delden B. V.)

20.8 parts of aliphatic hydrocarbon solvent (Exxsol D 40®, Deutsche Exxon Chemical GmbH)

4.16 parts of a metal drier (Jager Antihydro—Trockner®, E. Jäger KG)

0,70 parts of a PE—wax, 21% in solvent (Lanco Glidd AH® , G. M. Langer & Co)

The top coat is stabilized with 2% UVA (compound of the formula

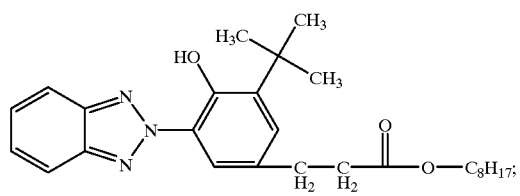

UV-Absorber from Ciba Specialty Chemicals) and 1% stabilizer according to the invention as indicated in the following table. All concentrations are by weight based on binder solids.

The topcoat is applied by brush (2 applications) on the impregnated pine panels and dried for 24 hours at room temperature after each application. The panels are exposed to accelerated weathering: (QUV, 8 h light at 70° C., 4 h condensation at 50° C., UV—A lamps). Gloss (60°) is measured according to DIN 67530 every 400h weathering. An unexposed pine panel with unstabilized top coat is used as reference. The results are presented in the following table.

TABLE

| Gloss (60°) after 2400 h exposure | |
|---|---|
| Unstabilized Topcoat | 25 |
| 2% UVA | 63 |
| 2% UVA + 1% cpd. of example 5 | 86 |

Initial gloss (60°) for all samples: 92–93

The results show a good gloss retainment achieved with the stabilizer of present invention.

EXAMPLE 26
Stabilization of a 2-coat metallic finish

The light-stabilizers to be tested are dissolved in 30 g of Solvesso®100 and tested in a clearcoat having the following composition (parts by weight):

| | |
|---|---|
| Synthacryl ® SC 303[1] | 27.51 |
| Synthacryl ® SC 370[2] | 23.34 |
| Maprenal ® 650[3] | 27.29 |
| Butyl acetate/Butanol (37/8) | 4.33 |
| Isobutanol | 4.87 |
| Solvesso ® 150[4] | 2.72 |
| Crystal Oil K-30[5] | 8.74 |
| Levelling assistant Baysilon ® MA[6] | 1.20 |
| | 100.00 |

[1]Acrylate resin, ®Hoechst AG; 65% solution in xylene/butanol (26:9)
[2]Acrylate resin, ®Hoechst AG; 75% solution in Solvesso ® 100[4]
[3]Melamine resin, ®Hoechst AG; 55% solution in isobutanol
[4]aromatic hydrocarbon mixture, boiling range 182–203° C. (Solvesso ® 150) or 161–178° C. (Solvesso ® 100); manufacturer: ®Esso
[5]aliphatic hydrocarbon mixture, boiling range: 145–200° C.; manufacturer: ®Shell
[6]1% in Solvesso ® 150; manufacturer: ®Bayer AG 1% of the stabilizer indicated in the following table and 1.5% of the UVA of example 25 are added to the clearcoat, based on the solids content of the varnish. For comparison, a clearcoat containing no light-stabilizers is used. The clearcoat is diluted with Solvesso® 100 to spray viscosity and is applied by spraying to a prepared aluminium panel (®Uniprime Epoxy, silver-metallic basecoat) which is baked at 130° C., for 30 minutes, to give a dry film thickness of 40–50 μm of clearcoat.

The samples are then weathered in an Atlas Xe-Wom weatherometer (CAM 180) in a cycle as follows: 40' UV-light, 20' light with rain (front), 60' light, 60' dark with rain (both sides), light at 70° C., dark at 40° C. (Filter: quartz/boro; 0.55 W/cm² at 340 nm).

The surface gloss (20° gloss as defined in DIN 67530) of the samples is then measured at regular intervals; high values indicate a good stabilization. The results are shown in the following table.

TABLE

| | 20° gloss (DIN 67530) after ... hours weathering | | |
|---|---|---|---|
| Light-stabilizer | 0 hours | 800 hours | 3200 hours |
| None | 94 | 33 | crack after 800 h |
| 1% cpd. of example 5 + 1.5% UVA | 92 | 92 | 72 |

What is claimed is:

1. A process for the preparation of a compound of the formula (I)

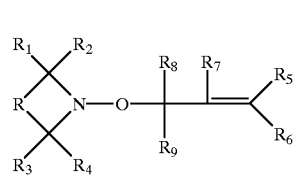

wherein $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl;

$R_5$, $R_6$, $R_7$, $R_8$ and $R_9$, independently of each other, are H; $C_1$–$C_8$alkyl; $C_2$–$C_8$alkenyl; $C_5$–$C_{12}$aryl; $C_1$–$C_4$haloalkyl; an electron withdrawing group selected from the group consisting of CN, nitro, halogen and —COOR$_{10}$, where $R_{10}$ is $C_1$–$C_{12}$alkyl or $C_5$–$C_{12}$cycloalkyl or $C_7$–$C_9$phenylalkyl or phenyl; or $R_5$, $R_4$, $R_7$, $R_8$ and $R_9$, independently of each other, are $C_6$–$C_{12}$aryl which is substituted by a residue selected from $C_1$–$C_4$alkyl, $C_1$–$C_4$alkoxy, halogen; and $R_7$ and $R_8$ together may also form a chemical bond; and the linking group R forms, together with the carbon atoms it is directly connected to and the nitrogen atom, a substituted, 5-, 6 or 7-membered cyclic ring structure;

wherein a compound of the formula (II)

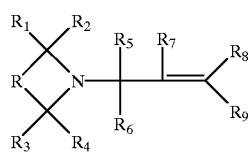

(II)

wherein all residues R and $R_1$–$R_9$ are as defined for formula (I), is oxidized.

2. A process according to claim 1, wherein the oxidation reaction is carried out in the presence of a solvent and an oxidant selected from oxygen, peroxides, nitrates, permanganates and chlorates.

3. A process according to claim 1 for the preparation of a compound of formula (I) by oxidation of a compound of formula (II), wherein $R_1$, $R_2$, $R_3$ and $R_4$, independently of each other, are $C_1$–$C_8$alkyl or $C_1$–$C_5$hydroxyalkyl, or $R_1$ and $R_2$ together with the carbon atom they are attached to are $C_5$–$C_{12}$cycloalkyl, or $R_3$ and $R_4$ together with the carbon atom they are attached to are $C_5$–$C_{12}$cycloalkyl;

$R_5$, $R_6$, $R_7$, $R_8$ and $R_9$, independently of each other, are H, $C_1$–$C_8$alkyl, $C_3$–$C_8$alkenyl, $C_5$–$C_{12}$aryl, an electron withdrawing group selected from the group consisting of CN, nitro, halogen and —COOR$_{10}$, where $R_{10}$ is $C_1$–$C_{12}$alkyl or $C_5$–$C_{12}$cycloalkyl or $C_7$–$C_9$phenylalkyl or phenyl; or $R_5$, $R_6$, $R_7$, $R_8$ and $R_9$, independently of each other, are $C_6$–$C_{12}$aryl which is substituted by $C_1$–$C_4$alkyl, $C_1$–$C_4$alkoxy, halogen; and R forms together with the two carbon atoms and the nitrogen atom, a substituted, 6-membered cyclic ring structure.

4. A process according to claim 1, wherein in the compounds of formulae (I) and (II)

$R_1$, $R_2$, $R_3$ and $R_4$ independently preferably are methyl or ethyl, $R_5$ and $R_6$ independently are H or methyl, and $R_7$, $R_8$ and $R_9$ independently are $C_1$–$C_4$haloalkyl, phenyl, vinyl, nitro, CN, COOR$_{10}$, or $R_7$ and $R_8$ together form a chemical bond.

5. A process for the preparation of a compound of the formula (V)

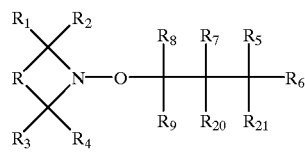

(V)

wherein

R, $R_1$, $R_2$, $R_3$ and $R_4$, $R_5$, $R_6$, and $R_9$ are as defined for formula (I) in claim 1, $R_7$ and $R_8$ are H, $C_1$–$C_8$alkyl, $C_3$–$C_8$alkenyl, $C_5$–$C_{12}$aryl, $C_1$–$C_4$haloalkyl, an electron withdrawing group selected from the group consisting of CN, nitro, halogen and —COOR$_{10}$, where $R_{10}$ is $C_1$–$C_{12}$alkyl or $C_5$–$C_{12}$cycloalkyl or $C_7$–$C_9$phenylalkyl or phenyl; or $R_7$ and $R_8$, independently of each other, are $C_6$–$C_{12}$aryl which is substituted by a residue selected from $C_1$–$C_4$alkyl, $C_1$–$C_4$alkoxy, halogen; and both of $R_{20}$ and $R_{21}$ are either hydrogen or halogen;

wherein a compound of the formula (II) as described in claim 1 is oxidized and the resulting intermediate of formula (I) is subjected to hydrogenation and/or halogenation.

6. A process according to claim 1, wherein the compound of the formula (I) conforms to the formula (Ia)

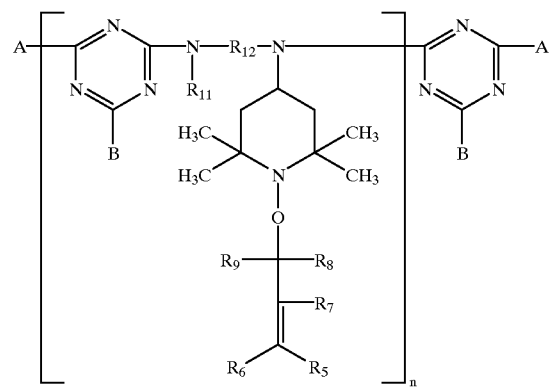

(Ia)

in which the index n ranges from 1 to 15;

$R_{12}$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_1$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic');

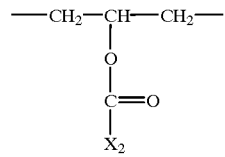

(Ib')

-continued

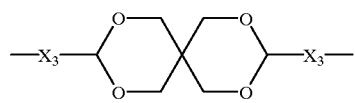
(Ic')

$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_{13}$, —$N(R_{14})R_{15}$) or a group of the formula (Id');

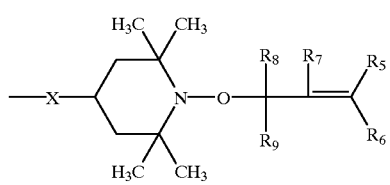
(Id')

$R_{13}$, $R_{14}$ and $R_{15}$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl) amino or a group of the formula (Ie');

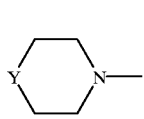
(Ie')

with Y being —O—, —$CH_2$—, —$CH_2CH_2$— or >N—$CH_3$, or —$N(R_{14})(R_{15})$ is additionally a group of the formula (Ie');

X is —O— or >N—$R_{16}$;

$R_{16}$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$allyl; tetrahydrofuryl, a group of the formula (If'),

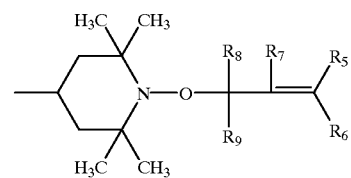
(If')

or $C_2$–$C_4$alkyl which is substituted in the 2, 3 or 4 position by —OH, $C_1$–$C_8$alkoxy, di($C_1$–$C_4$alkyl)amino or a group of the formula (Ie');

$R_{11}$ has one of the definitions given for $R_{16}$; and the radicals B have independently of one another one of the definitions given for A.

7. A process according to claim 5, wherein the compound of the formula (V) conforms to the formula (IIIb)

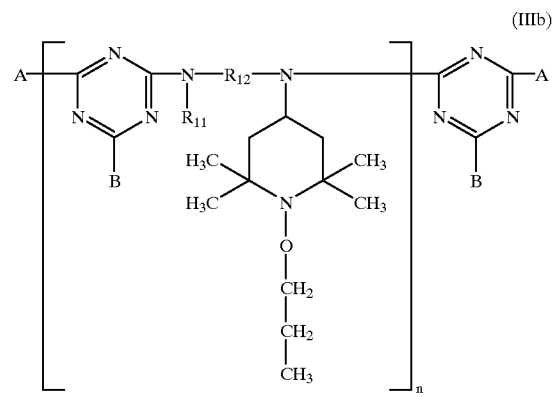
(IIIb)

in which the index n ranges from 1 to 15;

$R_{12}$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic');

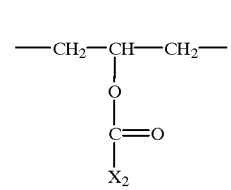
(Ib')

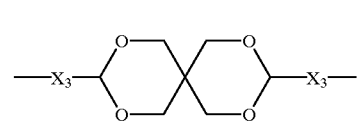
(Ic')

$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_{13}$, —$N(R_{14})(R_{15})$ or a group of the formula (IIId);

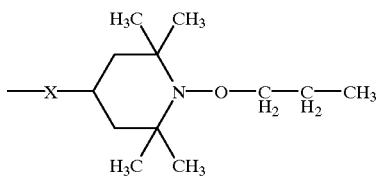
(IIId)

R₁₃, R₁₄ and R₁₅, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (Ie′);

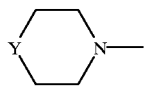
(Ie′)

with Y being —O—, —CH₂—, —CH₂CH₂— or >N—CH₃, or —N(R₁₄)(R₁₅) is additionally a group of the formula (Ie′);

X is —O— or >N—R₁₆;

R₁₆ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IIIf),

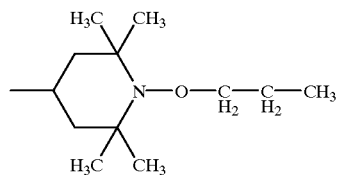
(IIIf)

or $C_2$–$C_4$alkyl which is substituted in the 2, 3 or 4 position by —OH, $C_1$–$C_8$alkoxy, di($C_1$–$C_4$alkyl)amino or a group of the formula (Ie′);

R₁₁ has one of the definitions given for R₁₆; and the radicals B have independently of one another one of the definitions given for A.

* * * * *

UNITED STATES PATENT AND TRADEMARK OFFICE
CERTIFICATE OF CORRECTION

PATENT NO. : 6,117,995
DATED : September 12, 2000
INVENTOR(S) : Alessandro Zedda et al.

It is certified that error appears in the above-identified patent and that said Letters Patent is hereby corrected as shown below:

<u>Title page,</u>
Item [30] should read, -- [30] Foreign Application Priority Data
                Feb. 25, 1998  [IT]  Italy...................M198A000366 --

Signed and Sealed this

Fourth Day of December, 2001

Attest:

NICHOLAS P. GODICI
Attesting Officer
*Acting Director of the United States Patent and Trademark Office*